United States Patent [19]

Matsushima et al.

[11] Patent Number: 6,048,972
[45] Date of Patent: *Apr. 11, 2000

[54] RECOMBINANT MATERIALS FOR PRODUCING HUMANIZED ANTI-IL-8 ANTIBODIES

[75] Inventors: Kouji Matsushima, Ishikawa; Yoshihiro Matsumoto, Shizuoka; Yoshiki Yamada, Shizuoka; Koh Sato, Shizuoka; Masayuki Tsuchiya, Shizuoka; Tatsumi Yamazaki, Shizuoka, all of Japan

[73] Assignee: Chugai Pharmaceutical Co., Ltd., Tokyo, Japan

[ * ] Notice: This patent is subject to a terminal disclaimer.

[21] Appl. No.: 08/880,142

[22] Filed: Jun. 20, 1997

Related U.S. Application Data

[63] Continuation of application No. 08/345,145, Nov. 28, 1994, abandoned, which is a continuation-in-part of application No. 08/303,841, Sep. 8, 1994, abandoned.

[30] Foreign Application Priority Data

Jul. 13, 1994 [JP] Japan .................................. 6-161481

[51] Int. Cl.$^7$ ............................. C12N 15/13; C12N 5/10; C12P 21/08
[52] U.S. Cl. ..................... 536/23.53; 435/69.6; 435/328; 435/332; 435/335
[58] Field of Search ........................ 536/23.53; 435/69.1, 435/326, 320.1, 252.3, 69.6, 440, 328, 335

[56] References Cited

U.S. PATENT DOCUMENTS 5,530,101 6/1996 Queen et al. .

FOREIGN PATENT DOCUMENTS

WO89/08665 9/1989 WIPO .
90/07861 7/1990 WIPO .

OTHER PUBLICATIONS

McElvaney, N.G. et al. Modulation of Airway Inflammation in Cystic Fibrosis, *J Clin Invest* (1992) 90:1296–1301.
Lynch III, J.P. et al. Neutorphilic Alveolitis in Idiopathic Pulmonary Fibrosis, *Am Rev Respir Dis* (1992) 145:1433–1439.
Donnelly, S.C. et al. Interleukin–8 and Development of Adult Respiratory Distress Syndrome in At-risk Patient Groups, *Lancet* (1993) 341:643–647.
Car, B.D. et al. Elevated IL–8 and MCP–1 in the Bronchoalveolar Lavage Fluid of Patients with Idiopathic Pulmonary Fibrosis and Pulmonary Sarcoidosis, *Am Rev Respir Crit Care Med* (1994) 149:655–659.
Antony, V.B. et al. Recruitment of Inflammatory Cells to the Pleural Space, *J Immunol* (1993) 151:7216–7223.
Takematsu, H. et al. Quantification of Chemotactic Peptides (C5a Anaphylatoxin and IL–8) in Psoriatic Lesional Skin, *Arch Dermatol* (1993) 129:74–80.

Brennan, F.M. et al. Detection of Interleukin 8 Biological Activity in Synovial Fluids from Patients with Rheumatoid Arthritis and Production of Interleukin 8 mRNA by Isolated Synovial Cells, *Eur J Immunol* (1990) 20:2141–2144.
Izzo, R.S. et al. Neutrophil–Activating Peptide (Interleukin–8) in Colonic Mucosa from Patients with Crohn's Disease, *Scand J Gastroenterol* (1993) 28:296–300.
Izzo, R.S. et al.Interleukin–8 and Neutrophil Markers in Colonic Mucosa from Patients with Ulcerative Colitis, *Am J Gastroenterol* (1992) 87:1447–1452.
Yoshimura, T., et al. Three Forms of Monocyte–Derived Neutrophil Chemotactic Factor (MDNCF) Distinguished by Different Lengths of the Amino–Terminal Sequence, *Mol Immunol* (1989) 26:87–93.
Ko, Y.C. et al. A Sensitive Enzyme–linked Immunosorbent Assay for Human Interleukin–8, *J Immunol Meth* (1992) 149:227–235.
Boylan, A.M. et al. Evidence of a Role for Mesothelial Cell–derived Interleukin 8 in the Pathogenesis of Asbestos–induced Pleurisy in Rabbits, *J Clin Invest* (1992) 89:1257–1267.
Mulligan, M.S. et al. Inhibition of Lung Inflammatory Reactions in Rats by an Anti–Human IL–8 Antibody, (*J Immunol* (1993) 150:5585–5595.
Harada, A. et al. Expression of Recombinant Rabbit IL–8 in *E. coli* and Establishment of the Essential Involvement of II–8 in Recruiting Neutrophils into Lipopolysaccharide–induced Inflammatory Site of Rabbit Skin, *International Immunol* (1993) 5:681–690.
Sekido, N. et al. Prevention of Lung Reperfusion Injury in Rabbits by a Monoclonal Antibody Against Interleukin–8, *Nature* (1993) 365:654–657.
Akahoshi, T. et al. Essential Involvement of Interluekin–8 in Neutrophil Recruitment in Rabbits with Acute Experimental Arthritis Induced by Lipopolysaccharide and Interleukin–1, *Lymphokine and Cytokine Res* (1994) 13:113–116.
LoBuglio, A.F. et al. Mouse/human Chimeric Monoclonal Antibody in Man: Kinetics and Immune Response, *Proc Natl Acad Sci USA* (1989) 86:4220–4224.
Sato, K., et al. Reshaping a Human Antibody to Inhibit the Interleukin 6–dependent Tumor Cell Growth, *Cancer Res* (1993) 53:851–856.
Riechmann, L., et al. Reshaping Human Antibodies for Therapy *Nature* (1988) 332:323–327.
Verhoeyen, M., et al. Reshaping Human Antibodies: Grafting an Antilysozyme Activity, *Science* (1988) 239:1534–1536.

(List continued on next page.)

*Primary Examiner*—Christina Y. Chan
*Assistant Examiner*—Phillip Gambel
*Attorney, Agent, or Firm*—Morrison & Foerster LLP

[57] ABSTRACT

Monoclonal antibodies immunospecific for the neutrophil chemotactic factor, IL-8, have been humanized by reshaping the variable regions to conform more closely to human counterparts. These antibodies are useful in immunoassays to detect IL-8 and as ligands on immunoaffinity columns for purification of human IL-8. In addition, the humanized antibodies have an antiinflammatory effect in patients.

36 Claims, 8 Drawing Sheets

OTHER PUBLICATIONS

Kettleborough, C.A., et al. Humanization of a Mouse Monoclonal Antibody by CDR–grafting: the Importance of Framework Residues on Loop Conformation, *Protein Engineering* (1991) 4:773–3783.

Maeda, H., et al. Construction of Reshaped Human Antibodies with HIV–neutralizing Activity, *Human Antibodies Hybridoma* (1991) 2:124–134.

Gorman, S.C., et al. Reshaping a Therapeutic CD4 Antibody, *Proc Natl Acad Sci USA* (1991) 88:4181–4185.

Tempest, P.R., et al. Reshaping a Human Monoclonal Antibody to Inhibit Human Respiratory Syncytial Virus Infection in vivo, *Bio/Technology* (1991) 9:266–271.

Co, M.S., et al., Humanized Antibodies for Antiviral Therapy, *Proc Natl Acad Sci USA* (1991) 88:2869–2873.

Carter, P., et al., Humanization of an Anti–p185$^{HER2}$ Antibody for Human Cancer Therapy, *Proc Natl Acad Sci USA* (1992) 89:4285–4289; and.

Co, M.S. et al. Chimeric and Humanized Antibodies with Specificity for the CD33 Antigen *J Immunol* (1992) 148:1149–1154.

Y. Matsumoto et al., *Humanization of Anti–human Interleukin–8 Antibody,* Nov. 28, 1994, from the 17th Annual Meeting of the Molecular Biology Society of Japan (Dec. 15, 1994) published Nov. 28, 1994.

Construction of DNA coding for reshaped human H chain V region

Construction of DNA coding for reshaped human L chain V region

SEQUENCE LISTING (1) GENERAL INFORMATION:

(iii) NUMBER OF SEQUENCES: 77

(2) INFORMATION FOR SEQ ID NO:1:

(i) SEQUENCE CHARACTERISTICS:
      (A) LENGTH: 40 base pairs
      (B) TYPE: nucleic acid
      (C) STRANDEDNESS: single
      (D) TOPOLOGY: linear (xi) SEQUENCE DESCRIPTION: SEQ ID NO:1:

ACTAGTCGAC ATGAAGTTGC CTGTTAGGCT GTTGGTGCTG     40

(2) INFORMATION FOR SEQ ID NO:2:

(i) SEQUENCE CHARACTERISTICS:
      (A) LENGTH: 39 base pairs
      (B) TYPE: nucleic acid
      (C) STRANDEDNESS: single
      (D) TOPOLOGY: linear (xi) SEQUENCE DESCRIPTION: SEQ ID NO:2:

ACTAGTCGAC ATGGAGWCAG ACACACTCCT GYTATGGGT     39

(2) INFORMATION FOR SEQ ID NO:3:

(i) SEQUENCE CHARACTERISTICS:

(A) LENGTH: 40 base pairs
            (B) TYPE: nucleic acid
            (C) STRANDEDNESS: single
            (D) TOPOLOGY: linear (xi) SEQUENCE DESCRIPTION: SEQ ID NO:3:

ACTAGTCGAC ATGAGTGTGC TCACTCAGGT CCTGGSGTTG                40

(2) INFORMATION FOR SEQ ID NO:4:

(i) SEQUENCE CHARACTERISTICS:
            (A) LENGTH: 43 base pairs
            (B) TYPE: nucleic acid
            (C) STRANDEDNESS: single
            (D) TOPOLOGY: linear (xi) SEQUENCE DESCRIPTION: SEQ ID NO:4:

ACTAGTCGAC ATGAGGRCCC CTGCTCAGWT TYTTGGMWTC TTG             43

(2) INFORMATION FOR SEQ ID NO:5:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (xi) SEQUENCE DESCRIPTION: SEQ ID NO:5:

ACTAGTCGAC ATGGATTTWC AGGTGCAGAT TWTCAGCTTC                40

(2) INFORMATION FOR SEQ ID NO:6:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (xi) SEQUENCE DESCRIPTION: SEQ ID NO:6:

ACTAGTCGAC ATGAGGTKCY YTGYTSAGYT YCTGRGG                   37

(2) INFORMATION FOR SEQ ID NO:7:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (xi) SEQUENCE DESCRIPTION: SEQ ID NO:7:

ACTAGTCGAC ATGGGCWTCA AGATGGAGTC ACAKWYYCWG G               41

(2) INFORMATION FOR SEQ ID NO:8:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (xi) SEQUENCE DESCRIPTION: SEQ ID NO:8:

ACTAGTCGAC ATGTGGGGAY CTKTTTYCMM TTTTTCAATT G               41

(2) INFORMATION FOR SEQ ID NO:9:

(i) SEQUENCE CHARACTERISTICS:
            (A) LENGTH: 35 base pairs (B) TYPE: nucleic acid
        (C) STRANDEDNESS: single
        (D) TOPOLOGY: linear (xi) SEQUENCE DESCRIPTION: SEQ ID NO:9:

ACTAGTCGAC ATGGTRTCCW CASCTCAGTT CCTTG                              35

(2) INFORMATION FOR SEQ ID NO:10:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:10:

ACTAGTCGAC ATGTATATAT GTTTGTTGTC TATTTCT                            37

(2) INFORMATION FOR SEQ ID NO:11:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:11:

ACTAGTCGAC ATGGAAGCCC CAGCTCAGCT TCTCTTCC                           38

(2) INFORMATION FOR SEQ ID NO:12:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:12:

GGATCCCGGG TGGATGGTGG GAAGATG                                       27

(2) INFORMATION FOR SEQ ID NO:13:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:13:

ACTAGTCGAC ATGAAATGCA GCTGGGTCAT STTCTTC                            37

(2) INFORMATION FOR SEQ ID NO:14:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:14:

ACTAGTCGAC ATGGGATGGA GCTRTATCAT SYTCTT                             36

(2) INFORMATION FOR SEQ ID NO:15:

(i) SEQUENCE CHARACTERISTICS:
        (A) LENGTH: 37 base pairs
        (B) TYPE: nucleic acid (C) STRANDEDNESS: single
        (D) TOPOLOGY: linear (xi) SEQUENCE DESCRIPTION: SEQ ID NO:15:

ACTAGTCGAC ATGAAGWTGT GGTTAAACTG GGTTTTT                                    37

(2) INFORMATION FOR SEQ ID NO:16:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:16:

ACTAGTCGAC ATGRACTTTG GGYTCAGCTT GRTTT                                      35

(2) INFORMATION FOR SEQ ID NO:17:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:17:

ACTAGTCGAC ATGGACTCCA GGCTCAATTT AGTTTTCCTT                                 40

(2) INFORMATION FOR SEQ ID NO:18:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:18:

ACTAGTCGAC ATGGCTGTCY TRGSGCTRCT CTTCTGC                                    37

(2) INFORMATION FOR SEQ ID NO:19:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:19:

ACTAGTCGAC ATGGRATGGA GCKGGRTCTT TMTCTT                                     36

(2) INFORMATION FOR SEQ ID NO:20:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:20:

ACTAGTCGAC ATGAGAGTGC TGATTCTTTT GTG                                        33

(2) INFORMATION FOR SEQ ID NO:21:

(i) SEQUENCE CHARACTERISTICS:
        (A) LENGTH: 40 base pairs
        (B) TYPE: nucleic acid
        (C) STRANDEDNESS: single (D) TOPOLOGY: linear (xi) SEQUENCE DESCRIPTION: SEQ ID NO:21:

ACTAGTCGAC ATGGMTTGGG TGTGGAMCTT GCTATTCCTG                    40

(2) INFORMATION FOR SEQ ID NO:22:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (xi) SEQUENCE DESCRIPTION: SEQ ID NO:22:

ACTAGTCGAC ATGGGCAGAC TTACATTCTC ATTCCTG                       37

(2) INFORMATION FOR SEQ ID NO:23:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (xi) SEQUENCE DESCRIPTION: SEQ ID NO:23:

ACTAGTCGAC ATGGATTTTG GGCTGATTTT TTTTATTG                      38

(2) INFORMATION FOR SEQ ID NO:24:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (xi) SEQUENCE DESCRIPTION: SEQ ID NO:24:

ACTAGTCGAC ATGATGGTGT TAAGTCTTCT GTACCTG                       37

(2) INFORMATION FOR SEQ ID NO:25:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (xi) SEQUENCE DESCRIPTION: SEQ ID NO:25:

GGATCCCGGG CCAGTGGATA GACAGATG                                 28

(2) INFORMATION FOR SEQ ID NO:26:

(i) SEQUENCE CHARACTERISTICS:
            (A) LENGTH: 382 base pairs
            (B) TYPE: nucleic acid
            (C) STRANDEDNESS: double
            (D) TOPOLOGY: linear (ix) FEATURE:
            (A) NAME/KEY: CDS
            (B) LOCATION: 1..381

(ix) FEATURE:
            (A) NAME/KEY: mat_peptide
            (B) LOCATION: 61

(xi) SEQUENCE DESCRIPTION: SEQ ID NO:26:

ATG AGT GTG CTC ACT CAG GTC CTG GGG TTG CTG CTG CTG TGG CTT ACA     48
Met Ser Val Leu Thr Gln Val Leu Gly Leu Leu Leu Leu Trp Leu Thr

```
            -20                 -15                 -10                 -5
GGT GCC AGA TGT GAC ATC CAG ATG ACT CAG TCT CCA GCC TCC CTA TCT           96
Gly Ala Arg Cys Asp Ile Gln Met Thr Gln Ser Pro Ala Ser Leu Ser
                         1                   5                  10

GCA TCT GTG GGA GAA ACT GTC ACC ATC ACA TGT CGA GCA AGT GAG ATT          144
Ala Ser Val Gly Glu Thr Val Thr Ile Thr Cys Arg Ala Ser Glu Ile
             15                  20                  25

ATT TAC AGT TAT TTA GCA TGG TAT CAG CAG AAA CAG GGA AAA TCT CCT          192
Ile Tyr Ser Tyr Leu Ala Trp Tyr Gln Gln Lys Gln Gly Lys Ser Pro
         30                  35                  40

CAG CTC CTG GTC TAT AAT GCA AAA ACC TTA GCA GAT GGT GTG TCA TCA          240
Gln Leu Leu Val Tyr Asn Ala Lys Thr Leu Ala Asp Gly Val Ser Ser
 45                  50                  55                  60

AGG TTC AGT GGC AGT GGA TCA GGC ACA CAG TTT TCT CTG CGG ATC AGC          288
Arg Phe Ser Gly Ser Gly Ser Gly Thr Gln Phe Ser Leu Arg Ile Ser
                 65                  70                  75

AGC CTG CAG CCT GAA GAT TTT GGG AGT TAT TAC TGT CAA CAT CAT TTT          336
Ser Leu Gln Pro Glu Asp Phe Gly Ser Tyr Tyr Cys Gln His His Phe
             80                  85                  90

GGT TTT CCT CGG ACG TTC GGT GGA GGC ACC AAG CTG GAA CTC AAA              381
Gly Phe Pro Arg Thr Phe Gly Gly Gly Thr Lys Leu Glu Leu Lys
         95                 100                 105

C                                                                        382

(2) INFORMATION FOR SEQ ID NO:27:

(i) SEQUENCE CHARACTERISTICS:
         (A) LENGTH: 127 amino acids
         (B) TYPE: amino acid
         (D) TOPOLOGY: linear (ii) MOLECULE TYPE: protein (xi) SEQUENCE DESCRIPTION: SEQ ID NO:27:

Met Ser Val Leu Thr Gln Val Leu Gly Leu Leu Leu Leu Trp Leu Thr
-20                 -15                 -10                 -5

Gly Ala Arg Cys Asp Ile Gln Met Thr Gln Ser Pro Ala Ser Leu Ser
                 1                   5                  10

Ala Ser Val Gly Glu Thr Val Thr Ile Thr Cys Arg Ala Ser Glu Ile
         15                  20                  25

Ile Tyr Ser Tyr Leu Ala Trp Tyr Gln Gln Lys Gln Gly Lys Ser Pro
     30                  35                  40

Gln Leu Leu Val Tyr Asn Ala Lys Thr Leu Ala Asp Gly Val Ser Ser
 45                  50                  55                  60

Arg Phe Ser Gly Ser Gly Ser Gly Thr Gln Phe Ser Leu Arg Ile Ser
             65                  70                  75

Ser Leu Gln Pro Glu Asp Phe Gly Ser Tyr Tyr Cys Gln His His Phe
         80                  85                  90

Gly Phe Pro Arg Thr Phe Gly Gly Gly Thr Lys Leu Glu Leu Lys
     95                 100                 105

(2) INFORMATION FOR SEQ ID NO:28:

(i) SEQUENCE CHARACTERISTICS:
         (A) LENGTH: 424 base pairs
         (B) TYPE: nucleic acid
         (C) STRANDEDNESS: double
         (D) TOPOLOGY: linear (ix) FEATURE:
         (A) NAME/KEY: CDS
```

(B) LOCATION: 1..423

(ix) FEATURE:
    (A) NAME/KEY: mat_peptide
    (B) LOCATION: 58

(xi) SEQUENCE DESCRIPTION: SEQ ID NO:28:

```
ATG AAG TTG TGG TTA AAC TGG GTT TTT CTT GTG ACA CTT TTA AAT GGT       48
Met Lys Leu Trp Leu Asn Trp Val Phe Leu Val Thr Leu Leu Asn Gly
-19         -15                 -10                 -5

ATC CAG TGT GAG GTG AAA CTG GTG GAG TCT GGA GGA GGC TTG ATA CAG       96
Ile Gln Cys Glu Val Lys Leu Val Glu Ser Gly Gly Gly Leu Ile Gln
            1               5                   10

CCT GGG GAT TCT CTG AGA CTC TCC TGT GTA ACC TCT GGG TTC ACC TTC      144
Pro Gly Asp Ser Leu Arg Leu Ser Cys Val Thr Ser Gly Phe Thr Phe
        15                  20                  25

AGT GAT TAC TAC CTG AGC TGG GTC CGC CAG CCT CCA GGA AAG GCA CTT      192
Ser Asp Tyr Tyr Leu Ser Trp Val Arg Gln Pro Pro Gly Lys Ala Leu
30                  35                  40                  45

GAG TGG GTG GGT CTC ATT AGA AAC AAA GCC AAT GGT TAC ACA AGA GAG      240
Glu Trp Val Gly Leu Ile Arg Asn Lys Ala Asn Gly Tyr Thr Arg Glu
                50                  55                  60

TAC AGT GCA TCT GTG AAG GGT CGG TTC ACC ATC TCC AGA GAT GAT TCC      288
Tyr Ser Ala Ser Val Lys Gly Arg Phe Thr Ile Ser Arg Asp Asp Ser
            65                  70                  75

CAA AGC ATC CTC TAT CTT CAA ATG AAC ACC CTG AGA GGT GAG GAC AGT      336
Gln Ser Ile Leu Tyr Leu Gln Met Asn Thr Leu Arg Gly Glu Asp Ser
        80                  85                  90

GCC ACT TAT TAC TGT GCA CGA GAG AAC TAT AGG TAC GAC GTA GAG CTT      384
Ala Thr Tyr Tyr Cys Ala Arg Glu Asn Tyr Arg Tyr Asp Val Glu Leu
    95                  100                 105

GCT TAC TGG GGC CAA GGG ACT CTG GTC ACT GTC TCT GCA G                424
Ala Tyr Trp Gly Gln Gly Thr Leu Val Thr Val Ser Ala
110                 115                 120
```

(2) INFORMATION FOR SEQ ID NO:29:

(i) SEQUENCE CHARACTERISTICS:
        (A) LENGTH: 141 amino acids
        (B) TYPE: amino acid
        (D) TOPOLOGY: linear (ii) MOLECULE TYPE: protein (xi) SEQUENCE DESCRIPTION: SEQ ID NO:29:

```
Met Lys Leu Trp Leu Asn Trp Val Phe Leu Val Thr Leu Leu Asn Gly
-19         -15                 -10                 -5

Ile Gln Cys Glu Val Lys Leu Val Glu Ser Gly Gly Gly Leu Ile Gln
            1               5                   10

Pro Gly Asp Ser Leu Arg Leu Ser Cys Val Thr Ser Gly Phe Thr Phe
        15                  20                  25

Ser Asp Tyr Tyr Leu Ser Trp Val Arg Gln Pro Pro Gly Lys Ala Leu
30                  35                  40                  45

Glu Trp Val Gly Leu Ile Arg Asn Lys Ala Asn Gly Tyr Thr Arg Glu
                50                  55                  60

Tyr Ser Ala Ser Val Lys Gly Arg Phe Thr Ile Ser Arg Asp Asp Ser
            65                  70                  75

Gln Ser Ile Leu Tyr Leu Gln Met Asn Thr Leu Arg Gly Glu Asp Ser
        80                  85                  90

Ala Thr Tyr Tyr Cys Ala Arg Glu Asn Tyr Arg Tyr Asp Val Glu Leu
    95                  100                 105
```

```
Ala Tyr Trp Gly Gln Gly Thr Leu Val Thr Val Ser Ala
110                 115                 120
```

(2) INFORMATION FOR SEQ ID NO:30:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:30:

ACAAAGCTTC CACCATGAGT GTGCTCACTC AGGT                                  34

(2) INFORMATION FOR SEQ ID NO:31:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:31:

GATAAGCTTC CACCATGAAG TTGTGGTTAA ACTGGGT                            37

(2) INFORMATION FOR SEQ ID NO:32:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:32:

CTTGGATCCA CTCACGTTTG AGTTCCAGCT TGGTGCC                            37

(2) INFORMATION FOR SEQ ID NO:33:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:33:

GTCGGATCCA CTCACCTGCA GAGACAGTGA CCAGAGT                            37

(2) INFORMATION FOR SEQ ID NO:34:

(i) SEQUENCE CHARACTERISTICS:
        (A) LENGTH: 137 base pairs
        (B) TYPE: nucleic acid
        (C) STRANDEDNESS: single
        (D) TOPOLOGY: linear (xi) SEQUENCE DESCRIPTION: SEQ ID NO:34:

TAAGCTTCCA CCATGGAGTT TGGGCTGAGC TGGGTTTTCC TTGTTGCTAT TTTAAAGGGT    60

GTCCAGTGTG AAGTGCAGCT GTTGGAGTCT GGGGGAGGCT TGGTCCAGCC TGGGGGTTCT   120

CTGAGACTCT CATGTGC                                                                 137

(2) INFORMATION FOR SEQ ID NO:35:

(i) SEQUENCE CHARACTERISTICS:
        (A) LENGTH: 143 base pairs
        (B) TYPE: nucleic acid (C) STRANDEDNESS: single
            (D) TOPOLOGY: linear (xi) SEQUENCE DESCRIPTION: SEQ ID NO:35:

GCACTGTACT CTCTTGTGTA ACCATTGGCT TTGTTTCTAA TGAGACCCAC CAACTCTAGC      60

CCTTTCCCTT GAGCTTGGCG GACCCAGCTC AGGTAGTAAT CACTGAAGGT GAATCCAGAG     120

GCAGCACATG AGAGTCTCAG AGA                                            143

(2) INFORMATION FOR SEQ ID NO:36:

(i) SEQUENCE CHARACTERISTICS:
            (A) LENGTH: 113 base pairs
            (B) TYPE: nucleic acid
            (C) STRANDEDNESS: single
            (D) TOPOLOGY: linear (xi) SEQUENCE DESCRIPTION: SEQ ID NO:36:

TACACAAGAG AGTACAGTGC ATCTGTGAAG GGCAGACTTA CCATCTCAAG AGAAGATTCA      60

AAGAACACGC TGTATCTGCA AATGAGCAGC CTGAAAACCG AAGACTTGGC CGT           113

(2) INFORMATION FOR SEQ ID NO:37:

(i) SEQUENCE CHARACTERISTICS:
            (A) LENGTH: 117 base pairs
            (B) TYPE: nucleic acid
            (C) STRANDEDNESS: single
            (D) TOPOLOGY: linear (xi) SEQUENCE DESCRIPTION: SEQ ID NO:37:

TCGGATCCAC TCACCTGAGG AGACGGTGAC CAGGGTTCCC TGGCCCCAGT AAGCAAGCTC      60

TACGTCGTAG CGATAGTTCT CTCTAGCACA GTAATACACG GCCAAGTCTT CGGTTTT       117

(2) INFORMATION FOR SEQ ID NO:38:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (xi) SEQUENCE DESCRIPTION: SEQ ID NO:38:

GATAAGCTTC CACCATGGAG TTTGGGCTGA GCTGGGT                               37

(2) INFORMATION FOR SEQ ID NO:39:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (xi) SEQUENCE DESCRIPTION: SEQ ID NO:39:

GTCGGATCCA CTCACCTGAG GAGACGGTGA C                                     31

(2) INFORMATION FOR SEQ ID NO:40:

(i) SEQUENCE CHARACTERISTICS:
            (A) LENGTH: 424 base pairs
            (B) TYPE: nucleic acid
            (C) STRANDEDNESS: double
            (D) TOPOLOGY: linear (ix) FEATURE:
            (A) NAME/KEY: CDS
            (B) LOCATION: 1..423

(ix) FEATURE:
      (A) NAME/KEY: mat_peptide
      (B) LOCATION: 58

(xi) SEQUENCE DESCRIPTION: SEQ ID NO:40:

| | | | | | | | | | | | | | | | | |
|---|---|---|---|---|---|---|---|---|---|---|---|---|---|---|---|---|
| ATG | GAG | TTT | GGG | CTG | AGC | TGG | GTT | TTC | CTT | GTT | GCT | ATT | TTA | AAG | GGT | 48 |
| Met | Glu | Phe | Gly | Leu | Ser | Trp | Val | Phe | Leu | Val | Ala | Ile | Leu | Lys | Gly | |
| -19 | | | | -15 | | | | -10 | | | | | -5 | | | |
| GTC | CAG | TGT | GAA | GTG | CAG | CTG | TTG | GAG | TCT | GGG | GGA | GGC | TTG | GTC | CAG | 96 |
| Val | Gln | Cys | Glu | Val | Gln | Leu | Leu | Glu | Ser | Gly | Gly | Gly | Leu | Val | Gln | |
| | | | 1 | | | | 5 | | | | | 10 | | | | |
| CCT | GGG | GGT | TCT | CTG | AGA | CTC | TCA | TGT | GCT | GCC | TCT | GGA | TTC | ACC | TTC | 144 |
| Pro | Gly | Gly | Ser | Leu | Arg | Leu | Ser | Cys | Ala | Ala | Ser | Gly | Phe | Thr | Phe | |
| | | 15 | | | | | 20 | | | | | 25 | | | | |
| AGT | GAT | TAC | TAC | CTG | AGC | TGG | GTC | CGC | CAA | GCT | CAA | GGG | AAA | GGG | CTA | 192 |
| Ser | Asp | Tyr | Tyr | Leu | Ser | Trp | Val | Arg | Gln | Ala | Gln | Gly | Lys | Gly | Leu | |
| 30 | | | | | 35 | | | | | 40 | | | | | 45 | |
| GAG | TTG | GTG | GGT | CTC | ATT | AGA | AAC | AAA | GCC | AAT | GGT | TAC | ACA | AGA | GAG | 240 |
| Glu | Leu | Val | Gly | Leu | Ile | Arg | Asn | Lys | Ala | Asn | Gly | Tyr | Thr | Arg | Glu | |
| | | | | 50 | | | | | 55 | | | | | 60 | | |
| TAC | AGT | GCA | TCT | GTG | AAG | GGC | AGA | CTT | ACC | ATC | TCA | AGA | GAA | GAT | TCA | 288 |
| Tyr | Ser | Ala | Ser | Val | Lys | Gly | Arg | Leu | Thr | Ile | Ser | Arg | Glu | Asp | Ser | |
| | | | 65 | | | | | 70 | | | | | 75 | | | |
| AAG | AAC | ACG | CTG | TAT | CTG | CAA | ATG | AGC | AGC | CTG | AAA | ACC | GAA | GAC | TTG | 336 |
| Lys | Asn | Thr | Leu | Tyr | Leu | Gln | Met | Ser | Ser | Leu | Lys | Thr | Glu | Asp | Leu | |
| | | 80 | | | | | 85 | | | | | 90 | | | | |
| GCC | GTG | TAT | TAC | TGT | GCT | AGA | GAG | AAC | TAT | CGC | TAC | GAC | GTA | GAG | CTT | 384 |
| Ala | Val | Tyr | Tyr | Cys | Ala | Arg | Glu | Asn | Tyr | Arg | Tyr | Asp | Val | Glu | Leu | |
| | | 95 | | | | | 100 | | | | | 105 | | | | |
| GCT | TAC | TGG | GGC | CAG | GGA | ACC | CTG | GTC | ACC | GTC | TCC | TCA | G | | | 424 |
| Ala | Tyr | Trp | Gly | Gln | Gly | Thr | Leu | Val | Thr | Val | Ser | Ser | | | | |
| 110 | | | | | 115 | | | | | 120 | | | | | | |

(2) INFORMATION FOR SEQ ID NO:41:

(i) SEQUENCE CHARACTERISTICS:
       (A) LENGTH: 141 amino acids
       (B) TYPE: amino acid
       (D) TOPOLOGY: linear (ii) MOLECULE TYPE: protein (xi) SEQUENCE DESCRIPTION: SEQ ID NO:41:

Met Glu Phe Gly Leu Ser Trp Val Phe Leu Val Ala Ile Leu Lys Gly
-19             -15                 -10                 -5

Val Gln Cys Glu Val Gln Leu Leu Glu Ser Gly Gly Gly Leu Val Gln
            1               5                   10

Pro Gly Gly Ser Leu Arg Leu Ser Cys Ala Ala Ser Gly Phe Thr Phe
        15                  20                  25

Ser Asp Tyr Tyr Leu Ser Trp Val Arg Gln Ala Gln Gly Lys Gly Leu
30                      35                  40                  45

Glu Leu Val Gly Leu Ile Arg Asn Lys Ala Asn Gly Tyr Thr Arg Glu
                50                  55                  60

Tyr Ser Ala Ser Val Lys Gly Arg Leu Thr Ile Ser Arg Glu Asp Ser
            65                  70                  75

Lys Asn Thr Leu Tyr Leu Gln Met Ser Ser Leu Lys Thr Glu Asp Leu
        80                  85                  90

Ala Val Tyr Tyr Cys Ala Arg Glu Asn Tyr Arg Tyr Asp Val Glu Leu
    95                  100                 105

```
Ala Tyr Trp Gly Gln Gly Thr Leu Val Thr Val Ser Ser
110                 115                 120
```

(2) INFORMATION FOR SEQ ID NO:42:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:42:

```
GGCTAGAGTG GGTGGGTCTC ATTAGAAACA AAGC                          34
```

(2) INFORMATION FOR SEQ ID NO:43:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:43:

```
GAGACCCACC CACTCTAGCC CTTTCCCTTG AGCTTG                        36
```

(2) INFORMATION FOR SEQ ID NO:44:

(i) SEQUENCE CHARACTERISTICS:
        (A) LENGTH: 424 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..423

(ix) FEATURE:
        (A) NAME/KEY: mat_peptide
        (B) LOCATION: 58

(xi) SEQUENCE DESCRIPTION: SEQ ID NO:44:

```
ATG GAG TTT GGG CTG AGC TGG GTT TTC CTT GTT GCT ATT TTA AAG GGT    48
Met Glu Phe Gly Leu Ser Trp Val Phe Leu Val Ala Ile Leu Lys Gly
-19             -15                 -10                 -5

GTC CAG TGT GAA GTG CAG CTG TTG GAG TCT GGG GGA GGC TTG GTC CAG    96
Val Gln Cys Glu Val Gln Leu Leu Glu Ser Gly Gly Gly Leu Val Gln
            1               5                   10

CCT GGG GGT TCT CTG AGA CTC TCA TGT GCT GCC TCT GGA TTC ACC TTC   144
Pro Gly Gly Ser Leu Arg Leu Ser Cys Ala Ala Ser Gly Phe Thr Phe
        15                  20                  25

AGT GAT TAC TAC CTG AGC TGG GTC CGC CAA GCT CAA GGG AAA GGG CTA   192
Ser Asp Tyr Tyr Leu Ser Trp Val Arg Gln Ala Gln Gly Lys Gly Leu
30                  35                  40                  45

GAG TGG GTG GGT CTC ATT AGA AAC AAA GCC AAT GGT TAC ACA AGA GAG   240
Glu Trp Val Gly Leu Ile Arg Asn Lys Ala Asn Gly Tyr Thr Arg Glu
                50                  55                  60

TAC AGT GCA TCT GTG AAG GGC AGA CTT ACC ATC TCA AGA GAA GAT TCA   288
Tyr Ser Ala Ser Val Lys Gly Arg Leu Thr Ile Ser Arg Glu Asp Ser
            65                  70                  75

AAG AAC ACG CTG TAT CTG CAA ATG AGC AGC CTG AAA ACC GAA GAC TTG   336
Lys Asn Thr Leu Tyr Leu Gln Met Ser Ser Leu Lys Thr Glu Asp Leu
        80                  85                  90

GCC GTG TAT TAC TGT GCT AGA GAG AAC TAT CGC TAC GAC GTA GAG CTT   384
Ala Val Tyr Tyr Cys Ala Arg Glu Asn Tyr Arg Tyr Asp Val Glu Leu
95                  100                 105
```

```
GCT TAC TGG GGC CAG GGA ACC CTG GTC ACC GTC TCC TCA G          424
Ala Tyr Trp Gly Gln Gly Thr Leu Val Thr Val Ser Ser
110                 115                 120
```

(2) INFORMATION FOR SEQ ID NO:45:

(i) SEQUENCE CHARACTERISTICS:
        (A) LENGTH: 141 amino acids
        (B) TYPE: amino acid
        (D) TOPOLOGY: linear (ii) MOLECULE TYPE: protein (xi) SEQUENCE DESCRIPTION: SEQ ID NO:45:

```
Met Glu Phe Gly Leu Ser Trp Val Phe Leu Val Ala Ile Leu Lys Gly
-19             -15                 -10                 -5

Val Gln Cys Glu Val Gln Leu Leu Glu Ser Gly Gly Gly Leu Val Gln
                1               5                   10

Pro Gly Gly Ser Leu Arg Leu Ser Cys Ala Ala Ser Gly Phe Thr Phe
            15                  20                  25

Ser Asp Tyr Tyr Leu Ser Trp Val Arg Gln Ala Gln Gly Lys Gly Leu
30                  35                  40                  45

Glu Trp Val Gly Leu Ile Arg Asn Lys Ala Asn Gly Tyr Thr Arg Glu
                50                  55                  60

Tyr Ser Ala Ser Val Lys Gly Arg Leu Thr Ile Ser Arg Glu Asp Ser
                65                  70                  75

Lys Asn Thr Leu Tyr Leu Gln Met Ser Ser Leu Lys Thr Glu Asp Leu
                80                  85                  90

Ala Val Tyr Tyr Cys Ala Arg Glu Asn Tyr Arg Tyr Asp Val Glu Leu
                95                  100                 105

Ala Tyr Trp Gly Gln Gly Thr Leu Val Thr Val Ser Ser
110                 115                 120
```

(2) INFORMATION FOR SEQ ID NO:46:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:46:

```
TGGGTCCGCC AAGCTCCAGG GAAAGGGCTA GA                             32
```

(2) INFORMATION FOR SEQ ID NO:47:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:47:

```
TCTAGCCCTT TCCCTGGAGC TTGGCGGACC CA                             32
```

(2) INFORMATION FOR SEQ ID NO:48:

(i) SEQUENCE CHARACTERISTICS:
        (A) LENGTH: 424 base pairs
        (B) TYPE: nucleic acid
        (C) STRANDEDNESS: double
        (D) TOPOLOGY: linear (ix) FEATURE:
    (A) NAME/KEY: CDS
    (B) LOCATION: 1..423

(ix) FEATURE:
    (A) NAME/KEY: mat_peptide
    (B) LOCATION: 58

(xi) SEQUENCE DESCRIPTION: SEQ ID NO:48:

| ATG | GAG | TTT | GGG | CTG | AGC | TGG | GTT | TTC | CTT | GTT | GCT | ATT | TTA | AAG | GGT | 48 |
| Met | Glu | Phe | Gly | Leu | Ser | Trp | Val | Phe | Leu | Val | Ala | Ile | Leu | Lys | Gly | |
| -19 | | | -15 | | | | -10 | | | | -5 | | | | | |

| GTC | CAG | TGT | GAA | GTG | CAG | CTG | TTG | GAG | TCT | GGG | GGA | GGC | TTG | GTC | CAG | 96 |
| Val | Gln | Cys | Glu | Val | Gln | Leu | Leu | Glu | Ser | Gly | Gly | Gly | Leu | Val | Gln | |
| | | | 1 | | | | 5 | | | | | 10 | | | | |

| CCT | GGG | GGT | TCT | CTG | AGA | CTC | TCA | TGT | GCT | GCC | TCT | GGA | TTC | ACC | TTC | 144 |
| Pro | Gly | Gly | Ser | Leu | Arg | Leu | Ser | Cys | Ala | Ala | Ser | Gly | Phe | Thr | Phe | |
| | 15 | | | | 20 | | | | 25 | | | | | | | |

| AGT | GAT | TAC | TAC | CTG | AGC | TGG | GTC | CGC | CAA | GCT | CCA | GGG | AAA | GGG | CTA | 192 |
| Ser | Asp | Tyr | Tyr | Leu | Ser | Trp | Val | Arg | Gln | Ala | Pro | Gly | Lys | Gly | Leu | |
| 30 | | | | 35 | | | | 40 | | | | | | | 45 | |

| GAG | TTG | GTG | GGT | CTC | ATT | AGA | AAC | AAA | GCC | AAT | GGT | TAC | ACA | AGA | GAG | 240 |
| Glu | Leu | Val | Gly | Leu | Ile | Arg | Asn | Lys | Ala | Asn | Gly | Tyr | Thr | Arg | Glu | |
| | | | 50 | | | | 55 | | | | | 60 | | | | |

| TAC | AGT | GCA | TCT | GTG | AAG | GGC | AGA | CTT | ACC | ATC | TCA | AGA | GAA | GAT | TCA | 288 |
| Tyr | Ser | Ala | Ser | Val | Lys | Gly | Arg | Leu | Thr | Ile | Ser | Arg | Glu | Asp | Ser | |
| | | 65 | | | | 70 | | | | 75 | | | | | | |

| AAG | AAC | ACG | CTG | TAT | CTG | CAA | ATG | AGC | AGC | CTG | AAA | ACC | GAA | GAC | TTG | 336 |
| Lys | Asn | Thr | Leu | Tyr | Leu | Gln | Met | Ser | Ser | Leu | Lys | Thr | Glu | Asp | Leu | |
| | 80 | | | | | 85 | | | | | 90 | | | | | |

| GCC | GTG | TAT | TAC | TGT | GCT | AGA | GAG | AAC | TAT | CGC | TAC | GAC | GTA | GAG | CTT | 384 |
| Ala | Val | Tyr | Tyr | Cys | Ala | Arg | Glu | Asn | Tyr | Arg | Tyr | Asp | Val | Glu | Leu | |
| | 95 | | | | 100 | | | | | 105 | | | | | | |

| GCT | TAC | TGG | GGC | CAG | GGA | ACC | CTG | GTC | ACC | GTC | TCC | TCA | G | | | 424 |
| Ala | Tyr | Trp | Gly | Gln | Gly | Thr | Leu | Val | Thr | Val | Ser | Ser | | | | |
| 110 | | | | 115 | | | | 120 | | | | | | | | |

(2) INFORMATION FOR SEQ ID NO:49:

(i) SEQUENCE CHARACTERISTICS:
        (A) LENGTH: 141 amino acids
        (B) TYPE: amino acid
        (D) TOPOLOGY: linear (ii) MOLECULE TYPE: protein (xi) SEQUENCE DESCRIPTION: SEQ ID NO:49:

| Met | Glu | Phe | Gly | Leu | Ser | Trp | Val | Phe | Leu | Val | Ala | Ile | Leu | Lys | Gly |
| -19 | | | | -15 | | | | | -10 | | | | | -5 | |

| Val | Gln | Cys | Glu | Val | Gln | Leu | Leu | Glu | Ser | Gly | Gly | Gly | Leu | Val | Gln |
| | | | 1 | | | | 5 | | | | | 10 | | | |

| Pro | Gly | Gly | Ser | Leu | Arg | Leu | Ser | Cys | Ala | Ala | Ser | Gly | Phe | Thr | Phe |
| | 15 | | | | 20 | | | | 25 | | | | | | |

| Ser | Asp | Tyr | Tyr | Leu | Ser | Trp | Val | Arg | Gln | Ala | Pro | Gly | Lys | Gly | Leu |
| 30 | | | | 35 | | | | 40 | | | | | | | 45 |

| Glu | Leu | Val | Gly | Leu | Ile | Arg | Asn | Lys | Ala | Asn | Gly | Tyr | Thr | Arg | Glu |
| | | | 50 | | | | 55 | | | | | 60 | | | |

| Tyr | Ser | Ala | Ser | Val | Lys | Gly | Arg | Leu | Thr | Ile | Ser | Arg | Glu | Asp | Ser |
| | | 65 | | | | 70 | | | | 75 | | | | | |

| Lys | Asn | Thr | Leu | Tyr | Leu | Gln | Met | Ser | Ser | Leu | Lys | Thr | Glu | Asp | Leu |
| | 80 | | | | | 85 | | | | | 90 | | | | |

```
Ala Val Tyr Tyr Cys Ala Arg Glu Asn Tyr Arg Tyr Asp Val Glu Leu
         95                 100                 105

Ala Tyr Trp Gly Gln Gly Thr Leu Val Thr Val Ser Ser
110                 115                 120
```

(2) INFORMATION FOR SEQ ID NO:50:

(i) SEQUENCE CHARACTERISTICS:
        (A) LENGTH: 424 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..423

(ix) FEATURE:
        (A) NAME/KEY: mat_peptide
        (B) LOCATION: 58

(xi) SEQUENCE DESCRIPTION: SEQ ID NO:50:

```
ATG GAG TTT GGG CTG AGC TGG GTT TTC CTT GTT GCT ATT TTA AAG GGT      48
Met Glu Phe Gly Leu Ser Trp Val Phe Leu Val Ala Ile Leu Lys Gly
-19             -15                 -10                 -5

GTC CAG TGT GAA GTG CAG CTG TTG GAG TCT GGG GGA GGC TTG GTC CAG      96
Val Gln Cys Glu Val Gln Leu Leu Glu Ser Gly Gly Gly Leu Val Gln
             1               5                  10

CCT GGG GGT TCT CTG AGA CTC TCA TGT GCT GCC TCT GGA TTC ACC TTC     144
Pro Gly Gly Ser Leu Arg Leu Ser Cys Ala Ala Ser Gly Phe Thr Phe
         15                  20                 25

AGT GAT TAC TAC CTG AGC TGG GTC CGC CAA GCT CCA GGG AAA GGG CTA     192
Ser Asp Tyr Tyr Leu Ser Trp Val Arg Gln Ala Pro Gly Lys Gly Leu
 30                 35                  40                  45

GAG TGG GTG GGT CTC ATT AGA AAC AAA GCC AAT GGT TAC ACA AGA GAG     240
Glu Trp Val Gly Leu Ile Arg Asn Lys Ala Asn Gly Tyr Thr Arg Glu
                 50                  55                  60

TAC AGT GCA TCT GTG AAG GGC AGA CTT ACC ATC TCA AGA GAA GAT TCA     288
Tyr Ser Ala Ser Val Lys Gly Arg Leu Thr Ile Ser Arg Glu Asp Ser
             65                  70                  75

AAG AAC ACG CTG TAT CTG CAA ATG AGC AGC CTG AAA ACC GAA GAC TTG     336
Lys Asn Thr Leu Tyr Leu Gln Met Ser Ser Leu Lys Thr Glu Asp Leu
         80                  85                  90

GCC GTG TAT TAC TGT GCT AGA GAG AAC TAT CGC TAC GAC GTA GAG CTT     384
Ala Val Tyr Tyr Cys Ala Arg Glu Asn Tyr Arg Tyr Asp Val Glu Leu
     95                 100                 105

GCT TAC TGG GGC CAG GGA ACC CTG GTC ACC GTC TCC TCA G               424
Ala Tyr Trp Gly Gln Gly Thr Leu Val Thr Val Ser Ser
110                 115                 120
```

(2) INFORMATION FOR SEQ ID NO:51:

(i) SEQUENCE CHARACTERISTICS:
        (A) LENGTH: 141 amino acids
        (B) TYPE: amino acid
        (D) TOPOLOGY: linear (ii) MOLECULE TYPE: protein (xi) SEQUENCE DESCRIPTION: SEQ ID NO:51:

```
Met Glu Phe Gly Leu Ser Trp Val Phe Leu Val Ala Ile Leu Lys Gly
-19             -15                 -10                 -5

Val Gln Cys Glu Val Gln Leu Leu Glu Ser Gly Gly Gly Leu Val Gln
             1               5                  10
```

```
Pro Gly Gly Ser Leu Arg Leu Ser Cys Ala Ala Ser Gly Phe Thr Phe
    15                  20                  25

Ser Asp Tyr Tyr Leu Ser Trp Val Arg Gln Ala Pro Gly Lys Gly Leu
30                  35                  40                  45

Glu Trp Val Gly Leu Ile Arg Asn Lys Ala Asn Gly Tyr Thr Arg Glu
                50                  55                  60

Tyr Ser Ala Ser Val Lys Gly Arg Leu Thr Ile Ser Arg Glu Asp Ser
            65                  70                  75

Lys Asn Thr Leu Tyr Leu Gln Met Ser Ser Leu Lys Thr Glu Asp Leu
        80                  85                  90

Ala Val Tyr Tyr Cys Ala Arg Glu Asn Tyr Arg Tyr Asp Val Glu Leu
    95                  100                 105

Ala Tyr Trp Gly Gln Gly Thr Leu Val Thr Val Ser Ser
110                 115                 120
```

(2) INFORMATION FOR SEQ ID NO:52:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:52:

TGGGTCCGCC AACCTCCAGG GAAAGG                                        26

(2) INFORMATION FOR SEQ ID NO:53:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:53:

CCTTTCCCTG GAGGTTGGCG GACCCA                                        26

(2) INFORMATION FOR SEQ ID NO:54:

(i) SEQUENCE CHARACTERISTICS:
        (A) LENGTH: 424 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..423

(ix) FEATURE:
        (A) NAME/KEY: mat_peptide
        (B) LOCATION: 58

(xi) SEQUENCE DESCRIPTION: SEQ ID NO:54:

```
ATG GAG TTT GGG CTG AGC TGG GTT TTC CTT GTT GCT ATT TTA AAG GGT        48
Met Glu Phe Gly Leu Ser Trp Val Phe Leu Val Ala Ile Leu Lys Gly
-19             -15                 -10                 -5

GTC CAG TGT GAA GTG CAG CTG TTG GAG TCT GGG GGA GGC TTG GTC CAG        96
Val Gln Cys Glu Val Gln Leu Leu Glu Ser Gly Gly Gly Leu Val Gln
            1               5                   10

CCT GGG GGT TCT CTG AGA CTC TCA TGT GCT GCC TCT GGA TTC ACC TTC       144
Pro Gly Gly Ser Leu Arg Leu Ser Cys Ala Ala Ser Gly Phe Thr Phe
    15                  20                  25

AGT GAT TAC TAC CTG AGC TGG GTC CGC CAA CCT CCA GGG AAA GGG CTA       192
```

```
Ser Asp Tyr Tyr Leu Ser Trp Val Arg Gln Pro Pro Gly Lys Gly Leu
 30                  35                  40                  45

GAG TGG GTG GGT CTC ATT AGA AAC AAA GCC AAT GGT TAC ACA AGA GAG        240
Glu Trp Val Gly Leu Ile Arg Asn Lys Ala Asn Gly Tyr Thr Arg Glu
             50                  55                  60

TAC AGT GCA TCT GTG AAG GGC AGA CTT ACC ATC TCA AGA GAA GAT TCA        288
Tyr Ser Ala Ser Val Lys Gly Arg Leu Thr Ile Ser Arg Glu Asp Ser
                 65                  70                  75

AAG AAC ACG CTG TAT CTG CAA ATG AGC AGC CTG AAA ACC GAA GAC TTG        336
Lys Asn Thr Leu Tyr Leu Gln Met Ser Ser Leu Lys Thr Glu Asp Leu
             80                  85                  90

GCC GTG TAT TAC TGT GCT AGA GAG AAC TAT CGC TAC GAC GTA GAG CTT        384
Ala Val Tyr Tyr Cys Ala Arg Glu Asn Tyr Arg Tyr Asp Val Glu Leu
         95                 100                 105

GCT TAC TGG GGC CAG GGA ACC CTG GTC ACC GTC TCC TCA G                  424
Ala Tyr Trp Gly Gln Gly Thr Leu Val Thr Val Ser Ser
110                 115                 120

(2) INFORMATION FOR SEQ ID NO:55:

(i) SEQUENCE CHARACTERISTICS:
        (A) LENGTH: 141 amino acids
        (B) TYPE: amino acid
        (D) TOPOLOGY: linear (ii) MOLECULE TYPE: protein (xi) SEQUENCE DESCRIPTION: SEQ ID NO:55:

Met Glu Phe Gly Leu Ser Trp Val Phe Leu Val Ala Ile Leu Lys Gly
-19             -15                 -10                  -5

Val Gln Cys Glu Val Gln Leu Leu Glu Ser Gly Gly Gly Leu Val Gln
              1               5                  10

Pro Gly Gly Ser Leu Arg Leu Ser Cys Ala Ala Ser Gly Phe Thr Phe
         15                  20                  25

Ser Asp Tyr Tyr Leu Ser Trp Val Arg Gln Pro Pro Gly Lys Gly Leu
 30                  35                  40                  45

Glu Trp Val Gly Leu Ile Arg Asn Lys Ala Asn Gly Tyr Thr Arg Glu
             50                  55                  60

Tyr Ser Ala Ser Val Lys Gly Arg Leu Thr Ile Ser Arg Glu Asp Ser
                 65                  70                  75

Lys Asn Thr Leu Tyr Leu Gln Met Ser Ser Leu Lys Thr Glu Asp Leu
             80                  85                  90

Ala Val Tyr Tyr Cys Ala Arg Glu Asn Tyr Arg Tyr Asp Val Glu Leu
         95                 100                 105

Ala Tyr Trp Gly Gln Gly Thr Leu Val Thr Val Ser Ser
110                 115                 120

(2) INFORMATION FOR SEQ ID NO:56:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:56:

CAAGCTCCAG GGAAAGCGCT AGAGTGGGT                                         29

(2) INFORMATION FOR SEQ ID NO:57:

(i) SEQUENCE CHARACTERISTICS:
```

```
          (A) LENGTH: 29 base pairs
          (B) TYPE: nucleic acid
          (C) STRANDEDNESS: single
          (D) TOPOLOGY: linear (xi) SEQUENCE DESCRIPTION: SEQ ID NO:57:

ACCCACTCTA GCGCTTTCCC TGGAGCTTG                                              29

(2) INFORMATION FOR SEQ ID NO:58:

(i) SEQUENCE CHARACTERISTICS:
          (A) LENGTH: 424 base pairs
          (B) TYPE: nucleic acid
          (C) STRANDEDNESS: double
          (D) TOPOLOGY: linear (ix) FEATURE:
          (A) NAME/KEY: CDS
          (B) LOCATION: 1..423

(ix) FEATURE:
          (A) NAME/KEY: mat_peptide
          (B) LOCATION: 58

(xi) SEQUENCE DESCRIPTION: SEQ ID NO:58:

ATG GAG TTT GGG CTG AGC TGG GTT TTC CTT GTT GCT ATT TTA AAG GGT              48
Met Glu Phe Gly Leu Ser Trp Val Phe Leu Val Ala Ile Leu Lys Gly
-19             -15                 -10                 -5

GTC CAG TGT GAA GTG CAG CTG TTG GAG TCT GGG GGA GGC TTG GTC CAG              96
Val Gln Cys Glu Val Gln Leu Leu Glu Ser Gly Gly Gly Leu Val Gln
                 1               5                  10

CCT GGG GGT TCT CTG AGA CTC TCA TGT GCT GCC TCT GGA TTC ACC TTC             144
Pro Gly Gly Ser Leu Arg Leu Ser Cys Ala Ala Ser Gly Phe Thr Phe
         15                  20                  25

AGT GAT TAC TAC CTG AGC TGG GTC CGC CAA GCT CCA GGG AAA GCG CTA             192
Ser Asp Tyr Tyr Leu Ser Trp Val Arg Gln Ala Pro Gly Lys Ala Leu
30                  35                  40                  45

GAG TGG GTG GGT CTC ATT AGA AAC AAA GCC AAT GGT TAC ACA AGA GAG             240
Glu Trp Val Gly Leu Ile Arg Asn Lys Ala Asn Gly Tyr Thr Arg Glu
                 50                  55                  60

TAC AGT GCA TCT GTG AAG GGC AGA CTT ACC ATC TCA AGA GAA GAT TCA             288
Tyr Ser Ala Ser Val Lys Gly Arg Leu Thr Ile Ser Arg Glu Asp Ser
             65                  70                  75

AAG AAC ACG CTG TAT CTG CAA ATG AGC AGC CTG AAA ACC GAA GAC TTG             336
Lys Asn Thr Leu Tyr Leu Gln Met Ser Ser Leu Lys Thr Glu Asp Leu
         80                  85                  90

GCC GTG TAT TAC TGT GCT AGA GAG AAC TAT CGC TAC GAC GTA GAG CTT             384
Ala Val Tyr Tyr Cys Ala Arg Glu Asn Tyr Arg Tyr Asp Val Glu Leu
     95                  100                 105

GCT TAC TGG GGC CAG GGA ACC CTG GTC ACC GTC TCC TCA G                       424
Ala Tyr Trp Gly Gln Gly Thr Leu Val Thr Val Ser Ser
110                 115                 120

(2) INFORMATION FOR SEQ ID NO:59:

(i) SEQUENCE CHARACTERISTICS:
          (A) LENGTH: 141 amino acids
          (B) TYPE: amino acid
          (D) TOPOLOGY: linear (ii) MOLECULE TYPE: protein (xi) SEQUENCE DESCRIPTION: SEQ ID NO:59:

Met Glu Phe Gly Leu Ser Trp Val Phe Leu Val Ala Ile Leu Lys Gly
-19             -15                 -10                 -5
```

```
Val Gln Cys Glu Val Gln Leu Leu Glu Ser Gly Gly Gly Leu Val Gln
        1               5                   10
```

```
Pro Gly Gly Ser Leu Arg Leu Ser Cys Ala Ala Ser Gly Phe Thr Phe
         15                  20                  25
```

```
Ser Asp Tyr Tyr Leu Ser Trp Val Arg Gln Ala Pro Gly Lys Ala Leu
 30                  35                  40                  45
```

```
Glu Trp Val Gly Leu Ile Arg Asn Lys Ala Asn Gly Tyr Thr Arg Glu
             50                  55                  60
```

```
Tyr Ser Ala Ser Val Lys Gly Arg Leu Thr Ile Ser Arg Glu Asp Ser
                 65                  70                  75
```

```
Lys Asn Thr Leu Tyr Leu Gln Met Ser Ser Leu Lys Thr Glu Asp Leu
             80                  85                  90
```

```
Ala Val Tyr Tyr Cys Ala Arg Glu Asn Tyr Arg Tyr Asp Val Glu Leu
         95                 100                 105
```

```
Ala Tyr Trp Gly Gln Gly Thr Leu Val Thr Val Ser Ser
110                 115                 120
```

(2) INFORMATION FOR SEQ ID NO:60:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:60:

```
GTGAAGGGCA GATTTACCAT CTC                                              23
```

(2) INFORMATION FOR SEQ ID NO:61:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:61:

```
GAGATGGTAA ATCTGCCCTT CAC                                              23
```

(2) INFORMATION FOR SEQ ID NO:62:

(i) SEQUENCE CHARACTERISTICS:
        (A) LENGTH: 424 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..423

(ix) FEATURE:
        (A) NAME/KEY: mat_peptide
        (B) LOCATION: 58

(xi) SEQUENCE DESCRIPTION: SEQ ID NO:62:

```
ATG GAG TTT GGG CTG AGC TGG GTT TTC CTT GTT GCT ATT TTA AAG GGT         48
Met Glu Phe Gly Leu Ser Trp Val Phe Leu Val Ala Ile Leu Lys Gly
-19             -15                 -10                 -5
```

```
GTC CAG TGT GAA GTG CAG CTG TTG GAG TCT GGG GGA GGC TTG GTC CAG         96
Val Gln Cys Glu Val Gln Leu Leu Glu Ser Gly Gly Gly Leu Val Gln
        1               5                   10
```

```
CCT GGG GGT TCT CTG AGA CTC TCA TGT GCT GCC TCT GGA TTC ACC TTC        144
Pro Gly Gly Ser Leu Arg Leu Ser Cys Ala Ala Ser Gly Phe Thr Phe
```

```
                15                    20                    25
AGT GAT TAC TAC CTG AGC TGG GTC CGC CAA GCT CCA GGG AAA GGG CTA        192
Ser Asp Tyr Tyr Leu Ser Trp Val Arg Gln Ala Pro Gly Lys Gly Leu
 30                   35                    40                   45

GAG TGG GTG GGT CTC ATT AGA AAC AAA GCC AAT GGT TAC ACA AGA GAG        240
Glu Trp Val Gly Leu Ile Arg Asn Lys Ala Asn Gly Tyr Thr Arg Glu
                      50                    55                    60

TAC AGT GCA TCT GTG AAG GGC AGA TTT ACC ATC TCA AGA GAA GAT TCA        288
Tyr Ser Ala Ser Val Lys Gly Arg Phe Thr Ile Ser Arg Glu Asp Ser
                 65                    70                    75

AAG AAC ACG CTG TAT CTG CAA ATG AGC AGC CTG AAA ACC GAA GAC TTG        336
Lys Asn Thr Leu Tyr Leu Gln Met Ser Ser Leu Lys Thr Glu Asp Leu
             80                    85                    90

GCC GTG TAT TAC TGT GCT AGA GAG AAC TAT CGC TAC GAC GTA GAG CTT        384
Ala Val Tyr Tyr Cys Ala Arg Glu Asn Tyr Arg Tyr Asp Val Glu Leu
         95                    100                   105

GCT TAC TGG GGC CAG GGA ACC CTG GTC ACC GTC TCC TCA G                  424
Ala Tyr Trp Gly Gln Gly Thr Leu Val Thr Val Ser Ser
110                   115                   120
```

(2) INFORMATION FOR SEQ ID NO:63:

(i) SEQUENCE CHARACTERISTICS:
        (A) LENGTH: 141 amino acids
        (B) TYPE: amino acid
        (D) TOPOLOGY: linear (ii) MOLECULE TYPE: protein (xi) SEQUENCE DESCRIPTION: SEQ ID NO:63:

```
Met Glu Phe Gly Leu Ser Trp Val Phe Leu Val Ala Ile Leu Lys Gly
-19                 -15                   -10                  -5

Val Gln Cys Glu Val Gln Leu Leu Glu Ser Gly Gly Gly Leu Val Gln
                 1                     5                    10

Pro Gly Gly Ser Leu Arg Leu Ser Cys Ala Ala Ser Gly Phe Thr Phe
             15                    20                    25

Ser Asp Tyr Tyr Leu Ser Trp Val Arg Gln Ala Pro Gly Lys Gly Leu
 30                   35                    40                   45

Glu Trp Val Gly Leu Ile Arg Asn Lys Ala Asn Gly Tyr Thr Arg Glu
                      50                    55                    60

Tyr Ser Ala Ser Val Lys Gly Arg Phe Thr Ile Ser Arg Glu Asp Ser
                 65                    70                    75

Lys Asn Thr Leu Tyr Leu Gln Met Ser Ser Leu Lys Thr Glu Asp Leu
             80                    85                    90

Ala Val Tyr Tyr Cys Ala Arg Glu Asn Tyr Arg Tyr Asp Val Glu Leu
         95                    100                   105

Ala Tyr Trp Gly Gln Gly Thr Leu Val Thr Val Ser Ser
110                   115                   120
```

(2) INFORMATION FOR SEQ ID NO:64:

(i) SEQUENCE CHARACTERISTICS:
        (A) LENGTH: 424 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..423

(ix) FEATURE:

(A) NAME/KEY: mat_peptide
            (B) LOCATION: 58

(xi) SEQUENCE DESCRIPTION: SEQ ID NO:64:

ATG GAG TTT GGG CTG AGC TGG GTT TTC CTT GTT GCT ATT TTA AAG GGT        48
Met Glu Phe Gly Leu Ser Trp Val Phe Leu Val Ala Ile Leu Lys Gly
-19         -15                 -10                 -5

GTC CAG TGT GAA GTG CAG CTG TTG GAG TCT GGG GGA GGC TTG GTC CAG        96
Val Gln Cys Glu Val Gln Leu Leu Glu Ser Gly Gly Gly Leu Val Gln
          1               5                  10

CCT GGG GGT TCT CTG AGA CTC TCA TGT GCT GCC TCT GGA TTC ACC TTC       144
Pro Gly Gly Ser Leu Arg Leu Ser Cys Ala Ala Ser Gly Phe Thr Phe
     15                  20                  25

AGT GAT TAC TAC CTG AGC TGG GTC CGC CAA GCT CAA GGG AAA GGG CTA       192
Ser Asp Tyr Tyr Leu Ser Trp Val Arg Gln Ala Gln Gly Lys Gly Leu
 30              35                  40                  45

GAG TGG GTG GGT CTC ATT AGA AAC AAA GCC AAT GGT TAC ACA AGA GAG       240
Glu Trp Val Gly Leu Ile Arg Asn Lys Ala Asn Gly Tyr Thr Arg Glu
                  50                  55                  60

TAC AGT GCA TCT GTG AAG GGC AGA TTT ACC ATC TCA AGA GAA GAT TCA       288
Tyr Ser Ala Ser Val Lys Gly Arg Phe Thr Ile Ser Arg Glu Asp Ser
                 65                  70                  75

AAG AAC ACG CTG TAT CTG CAA ATG AGC AGC CTG AAA ACC GAA GAC TTG       336
Lys Asn Thr Leu Tyr Leu Gln Met Ser Ser Leu Lys Thr Glu Asp Leu
             80                  85                  90

GCC GTG TAT TAC TGT GCT AGA GAG AAC TAT CGC TAC GAC GTA GAG CTT       384
Ala Val Tyr Tyr Cys Ala Arg Glu Asn Tyr Arg Tyr Asp Val Glu Leu
         95                  100                 105

GCT TAC TGG GGC CAG GGA ACC CTG GTC ACC GTC TCC TCA G                 424
Ala Tyr Trp Gly Gln Gly Thr Leu Val Thr Val Ser Ser
110                 115                 120

(2) INFORMATION FOR SEQ ID NO:65:

(i) SEQUENCE CHARACTERISTICS:
          (A) LENGTH: 141 amino acids
          (B) TYPE: amino acid
          (D) TOPOLOGY: linear (ii) MOLECULE TYPE: protein (xi) SEQUENCE DESCRIPTION: SEQ ID NO:65:

Met Glu Phe Gly Leu Ser Trp Val Phe Leu Val Ala Ile Leu Lys Gly
-19         -15                 -10                 -5

Val Gln Cys Glu Val Gln Leu Leu Glu Ser Gly Gly Gly Leu Val Gln
          1               5                  10

Pro Gly Gly Ser Leu Arg Leu Ser Cys Ala Ala Ser Gly Phe Thr Phe
     15                  20                  25

Ser Asp Tyr Tyr Leu Ser Trp Val Arg Gln Ala Gln Gly Lys Gly Leu
 30              35                  40                  45

Glu Trp Val Gly Leu Ile Arg Asn Lys Ala Asn Gly Tyr Thr Arg Glu
                  50                  55                  60

Tyr Ser Ala Ser Val Lys Gly Arg Phe Thr Ile Ser Arg Glu Asp Ser
                 65                  70                  75

Lys Asn Thr Leu Tyr Leu Gln Met Ser Ser Leu Lys Thr Glu Asp Leu
             80                  85                  90

Ala Val Tyr Tyr Cys Ala Arg Glu Asn Tyr Arg Tyr Asp Val Glu Leu
         95                  100                 105

Ala Tyr Trp Gly Gln Gly Thr Leu Val Thr Val Ser Ser
110                 115                 120

(2) INFORMATION FOR SEQ ID NO:66:

(i) SEQUENCE CHARACTERISTICS:
        (A) LENGTH: 124 base pairs
        (B) TYPE: nucleic acid
        (C) STRANDEDNESS: single
        (D) TOPOLOGY: linear (xi) SEQUENCE DESCRIPTION: SEQ ID NO:66:

TTGAAGCTTC CACCATGGGA TGGAGCTGTA TCATCCTCTT CTTGGTAGCA ACAGCTACAG        60

GTGTCCACTC CGACATCCAG ATGACCCAGA GCCCAAGCAG CCTGAGCGCC AGCGTAGGTG       120

ACAG                                                                   124

(2) INFORMATION FOR SEQ ID NO:67:

(i) SEQUENCE CHARACTERISTICS:
        (A) LENGTH: 122 base pairs
        (B) TYPE: nucleic acid
        (C) STRANDEDNESS: single
        (D) TOPOLOGY: linear (xi) SEQUENCE DESCRIPTION: SEQ ID NO:67:

GCATTGTAGA TCAGCAGCTT TGGAGCCTTT CCTGGCTTCT GCTGGTACCA TGCTAAATAA        60

CTGTAAATAA TCTCGCTTGC TCGACAGGTG ATGGTCACTC TGTCACCTAC GCTGGCGCTC       120

AG                                                                     122

(2) INFORMATION FOR SEQ ID NO:68:

(i) SEQUENCE CHARACTERISTICS:
        (A) LENGTH: 121 base pairs
        (B) TYPE: nucleic acid
        (C) STRANDEDNESS: single
        (D) TOPOLOGY: linear (xi) SEQUENCE DESCRIPTION: SEQ ID NO:68:

AGCTGCTGAT CTACAATGCA AAAACCTTAG CAGATGGAGT GCCAAGCAGA TTCAGCGGTA        60

GCGGTAGCGG TACCGACTTC ACCTTCACCA TCAGCAGCCT CCAGCCAGAG GACATCGCTA       120

C                                                                      121

(2) INFORMATION FOR SEQ ID NO:69:

(i) SEQUENCE CHARACTERISTICS:
        (A) LENGTH: 106 base pairs
        (B) TYPE: nucleic acid
        (C) STRANDEDNESS: single
        (D) TOPOLOGY: linear (xi) SEQUENCE DESCRIPTION: SEQ ID NO:69:

GTAGGATCCA CTCACGTTTG ATTTCGACCT TGGTCCCTTG GCCGAACGTC CGAGGAAAAC        60

CAAAATGATG TTGGCAGTAG TAGGTAGCGA TGTCCTCTGG CTGGAG                     106

(2) INFORMATION FOR SEQ ID NO:70:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:70:

TTGAAGCTTC CACCATGGGA                                                   20

(2) INFORMATION FOR SEQ ID NO:71:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:71:

```
GTAGGATCCA CTCACGTTTG                                             20
```

(2) INFORMATION FOR SEQ ID NO:72:

(i) SEQUENCE CHARACTERISTICS:
        (A) LENGTH: 379 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..378

(ix) FEATURE:
        (A) NAME/KEY: mat_peptide
        (B) LOCATION: 58

(xi) SEQUENCE DESCRIPTION: SEQ ID NO:72:

```
ATG GGA TGG AGC TGT ATC ATC CTC TTC TTG GTA GCA ACA GCT ACA GGT    48
Met Gly Trp Ser Cys Ile Ile Leu Phe Leu Val Ala Thr Ala Thr Gly
-19             -15                 -10                 -5

GTC CAC TCC GAC ATC CAG ATG ACC CAG AGC CCA AGC AGC CTG AGC GCC    96
Val His Ser Asp Ile Gln Met Thr Gln Ser Pro Ser Ser Leu Ser Ala
             1               5                  10

AGC GTA GGT GAC AGA GTG ACC ATC ACC TGT CGA GCA AGC GAG ATT ATT   144
Ser Val Gly Asp Arg Val Thr Ile Thr Cys Arg Ala Ser Glu Ile Ile
     15                  20                  25

TAC AGT TAT TTA GCA TGG TAC CAG CAG AAG CCA GGA AAG GCT CCA AAG   192
Tyr Ser Tyr Leu Ala Trp Tyr Gln Gln Lys Pro Gly Lys Ala Pro Lys
 30              35                  40                  45

CTG CTG ATC TAC AAT GCA AAA ACC TTA GCA GAT GGA GTG CCA AGC AGA   240
Leu Leu Ile Tyr Asn Ala Lys Thr Leu Ala Asp Gly Val Pro Ser Arg
             50                  55                  60

TTC AGC GGT AGC GGT AGC GGT ACC GAC TTC ACC TTC ACC ATC AGC AGC   288
Phe Ser Gly Ser Gly Ser Gly Thr Asp Phe Thr Phe Thr Ile Ser Ser
                 65                  70                  75

CTC CAG CCA GAG GAC ATC GCT ACC TAC TAC TGC CAA CAT CAT TTT GGT   336
Leu Gln Pro Glu Asp Ile Ala Thr Tyr Tyr Cys Gln His His Phe Gly
             80                  85                  90

TTT CCT CGG ACG TTC GGC CAA GGG ACC AAG GTC GAA ATC AAA           378
Phe Pro Arg Thr Phe Gly Gln Gly Thr Lys Val Glu Ile Lys
         95                 100                 105

C                                                                 379
```

(2) INFORMATION FOR SEQ ID NO:73:

(i) SEQUENCE CHARACTERISTICS:
        (A) LENGTH: 126 amino acids
        (B) TYPE: amino acid
        (D) TOPOLOGY: linear (ii) MOLECULE TYPE: protein (xi) SEQUENCE DESCRIPTION: SEQ ID NO:73:

```
Met Gly Trp Ser Cys Ile Ile Leu Phe Leu Val Ala Thr Ala Thr Gly
-19             -15                 -10                 -5

Val His Ser Asp Ile Gln Met Thr Gln Ser Pro Ser Ser Leu Ser Ala
                 1              5                  10

Ser Val Gly Asp Arg Val Thr Ile Thr Cys Arg Ala Ser Glu Ile Ile
            15              20              25

Tyr Ser Tyr Leu Ala Trp Tyr Gln Gln Lys Pro Gly Lys Ala Pro Lys
30              35                  40              45

Leu Leu Ile Tyr Asn Ala Lys Thr Leu Ala Asp Gly Val Pro Ser Arg
                50              55                  60

Phe Ser Gly Ser Gly Ser Gly Thr Asp Phe Thr Phe Thr Ile Ser Ser
            65              70              75

Leu Gln Pro Glu Asp Ile Ala Thr Tyr Tyr Cys Gln His His Phe Gly
        80              85              90

Phe Pro Arg Thr Phe Gly Gln Gly Thr Lys Val Glu Ile Lys
        95              100             105
```

(2) INFORMATION FOR SEQ ID NO:74:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:74:

AGCGGTAGCG GTACCGACTA CACCTTCACC ATCAGCAG                     38

(2) INFORMATION FOR SEQ ID NO:75:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:75:

CTGCTGATGG TGAAGGTGTA GTCGGTACCG CTACCGCT                     38

(2) INFORMATION FOR SEQ ID NO:76:

(i) SEQUENCE CHARACTERISTICS:
        (A) LENGTH: 379 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..378

(ix) FEATURE:
        (A) NAME/KEY: mat_peptide
        (B) LOCATION: 58

(xi) SEQUENCE DESCRIPTION: SEQ ID NO:76:

```
ATG GGA TGG AGC TGT ATC ATC CTC TTC TTG GTA GCA ACA GCT ACA GGT      48
Met Gly Trp Ser Cys Ile Ile Leu Phe Leu Val Ala Thr Ala Thr Gly
-19             -15                 -10                 -5

GTC CAC TCC GAC ATC CAG ATG ACC CAG AGC CCA AGC AGC CTG AGC GCC      96
Val His Ser Asp Ile Gln Met Thr Gln Ser Pro Ser Ser Leu Ser Ala
                 1              5                   10

AGC GTA GGT GAC AGA GTG ACC ATC ACC TGT CGA GCA AGC GAG ATT ATT     144
Ser Val Gly Asp Arg Val Thr Ile Thr Cys Arg Ala Ser Glu Ile Ile
```

```
                    15                    20                    25
TAC AGT TAT TTA GCA TGG TAC CAG CAG AAG CCA GGA AAG GCT CCA AAG                192
Tyr Ser Tyr Leu Ala Trp Tyr Gln Gln Lys Pro Gly Lys Ala Pro Lys
    30                    35                    40                    45

CTG CTG ATC TAC AAT GCA AAA ACC TTA GCA GAT GGA GTG CCA AGC AGA                240
Leu Leu Ile Tyr Asn Ala Lys Thr Leu Ala Asp Gly Val Pro Ser Arg
                    50                    55                    60

TTC AGC GGT AGC GGT AGC GGT ACC GAC TAC ACC TTC ACC ATC AGC AGC                288
Phe Ser Gly Ser Gly Ser Gly Thr Asp Tyr Thr Phe Thr Ile Ser Ser
                65                    70                    75

CTC CAG CCA GAG GAC ATC GCT ACC TAC TAC TGC CAA CAT CAT TTT GGT                336
Leu Gln Pro Glu Asp Ile Ala Thr Tyr Tyr Cys Gln His His Phe Gly
            80                    85                    90

TTT CCT CGG ACG TTC GGC CAA GGG ACC AAG GTC GAA ATC AAA                        378
Phe Pro Arg Thr Phe Gly Gln Gly Thr Lys Val Glu Ile Lys
        95                    100                   105

C                                                                              379

(2) INFORMATION FOR SEQ ID NO:77:

(i) SEQUENCE CHARACTERISTICS:
        (A) LENGTH: 126 amino acids
        (B) TYPE: amino acid
        (D) TOPOLOGY: linear (ii) MOLECULE TYPE: protein (xi) SEQUENCE DESCRIPTION: SEQ ID NO:77:

Met Gly Trp Ser Cys Ile Ile Leu Phe Leu Val Ala Thr Ala Thr Gly
-19             -15                 -10                 -5

Val His Ser Asp Ile Gln Met Thr Gln Ser Pro Ser Ser Leu Ser Ala
            1                   5                   10

Ser Val Gly Asp Arg Val Thr Ile Thr Cys Arg Ala Ser Glu Ile Ile
        15                  20                  25

Tyr Ser Tyr Leu Ala Trp Tyr Gln Gln Lys Pro Gly Lys Ala Pro Lys
    30                    35                  40                45

Leu Leu Ile Tyr Asn Ala Lys Thr Leu Ala Asp Gly Val Pro Ser Arg
                50                    55                  60

Phe Ser Gly Ser Gly Ser Gly Thr Asp Tyr Thr Phe Thr Ile Ser Ser
                65                    70                  75

Leu Gln Pro Glu Asp Ile Ala Thr Tyr Tyr Cys Gln His His Phe Gly
            80                    85                  90

Phe Pro Arg Thr Phe Gly Gln Gly Thr Lys Val Glu Ile Lys
        95                    100                 105
```

RECOMBINANT MATERIALS FOR PRODUCING HUMANIZED ANTI-IL-8 ANTIBODIES

This application is a continuation of application Ser. No. 08/345,145, filed Nov. 28, 1994, now abandoned which is a continuation-in-part of U.S. Ser. No. 08/303,841 filed Sep. 8, 1994 now abandoned, the contents of which are incorporated herein by reference.

TECHNICAL FIELD

The invention relates to monoclonal antibodies which are humanized by modifying the framework structure that supports the determinant regions of the variable domains. More specifically, the invention relates to monoclonal antibodies immunospecific for human IL-8 that have humanized framework regions so as to be compatible with the human immune system and to intermediates for the production of such antibodies.

BACKGROUND ART

Human IL-8 is a cytokine which has variously been called neutrophil-activating protein, neutrophil chemotactic factor (NCF) and T-cell chemotactic factor. IL-8 can be secreted by several types of cells upon appropriate stimulation. IL-8 is secreted by activated monocytes and macrophages as well as by embryonic fibroblasts.

IL-8 is known to induce neutrophil migration and to activate functions of neutrophils such as degranulation, release of superoxide anion and adhesion to the endothelial cell monolayer. There are a number of conditions that are known to involve leukocyte infiltration into lesions. These include pulmonary diseases such as pulmonary cystic fibrosis, idiopathic pulmonary fibrosis, adult respiratory distress syndrome, sarcoidosis and empyema; dermal diseases such as psoriasis, rheumatoid arthritis, Crohn's Disease; and in inflammatory bowel disease (McElvaney, N. G. et al. *J Clin Invest* (1992) 90:1296–1301; Lynch III, J. P. et al. *Am Rev Respir Dis* (1992) 145:1433–1439; Donnelly, S. C. et al. *Lancet* (1993) 341:643–647; Car, B. D. et al. *Am J Respir Crit Care Med* (1994) 149:655–659; Antony, V. B. et al. *J Immunol* (1993) 151:7216–7223; Takematsu, H. et al. *Arch Dermatol* (1993) 129:74–80; Brennan, F. M. et al. *Eur J Immunol* (1990) 20:2141–2144; Izzo, R. S. et al. *Scand J Gastroenterol* (1993) 28:296–300; Izzo, R. S. et al. *Am J Gastroenterol* (1992) 87:1447–1452).

The amino acid sequence characterizing human IL-8 was described by Matsushima, et al. in PCT application WO89/08665. More recently, Yoshimura, T., et al. in *Mol Immunol* (1989) 26:87–93 showed that monocyte-derived IL-8 was evidently variably processed at the N-terminus and that the IL-8 originally disclosed by Matsushima et al. was accompanied by two forms of the factor which had seven or five additional amino acids at the N-terminus. The longest form accounted for about 8%, the next longest form for about 47%, and the shortest form for about 45% of the total IL-8 derived from monocytes.

WO89/08665 also reports the production of murine monoclonal antibodies immunoreactive with this protein (called neutrophil chemotactic factor in this publication). An additional murine monoclonal antibody immunospecific for IL-8 and designated WS-4 was prepared and reported by Ko, Y. C. et al. *J Immunol Meth* (1992) 149:227–235. DNA encoding heavy and light chains of this antibody was recovered from the hybridoma which produced it, as described below. Additional murine-derived antibodies to human IL-8 were reported by Boylan, A. M. et al. *J Clin Invest* (1992) 89:1257–1267 (A5.12.14); in PCT application WO92/04372 (Anti-Pep1 AND Anti-Pep3) and by Mulligan, M. S. et al. (*J Immunol* (1993) 150:5585–5595) (DM/C7).

WS-4 has been shown to inhibit the binding of rabbit IL-8 to rabbit neutrophils by Harada, A. et al. *International Immunol* (1993) 5:681–690. Administration of WS-4 to rabbits also reduced ischemia/reperfusion injury in the lung (Sekido, N. et al. *Nature* (1993) 365:654–657); reduced LPS-induced dermatitis (Harada et al. (supra)); and ameliorated LPS or IL-1 induced arthritis (Akahoshi, T. et al. *Lymphokine and Cytokine Res* (1994) 13:113–116). Administration of DM/C7 intratracheally to rats was protective with respect to inflammatory lung injury (Mulligan, M. S., et al. (supra)). Thus, animal models have demonstrated that antibodies to IL-8 are effective in treating diseases and conditions which are characterized by inflammation.

It would therefore be useful to have antibodies immunoreactive with human IL-8 which would be compatible with the human immune system so that these antibodies could be used as therapeutic agents. It is known that murine antibodies are highly immunogenic in humans, thus limiting their value as therapeutic agents. Furthermore, murine antibodies have low circulating half-lives in humans. It would be ideal to prepare anti-IL-8 antibodies which do not raise antibodies against themselves in human patients and which retain their effectiveness against human IL-8.

Other nonhuman antibodies have been "humanized" with varying degrees of success in the past. In a straightforward and simple but incomplete approach, chimeric antibodies are prepared, generally using recombinant techniques, which contain nonhuman variable regions and human constant regions. This eliminates the constant region as an immunogen in human patients, but the possibility of an immune response to the foreign variable region remains (LoBuglio, A. F. et al. *Proc Natl Acad Sci USA* (1989) 86:4220–4224).

A more sophisticated approach focuses not only on providing human-derived constant regions, but modifying the variable regions as well so as to reshape them as closely as possible to human form. It is known that the variable regions of both heavy and light chains contain three complementarity-determining regions (CDRs) which vary in response to the antigens in question and determine binding capability, flanked by four framework regions (FRs) which are relatively conserved in a given species and which putatively provide a scaffolding for the CDRs. When nonhuman antibodies are prepared with respect to a particular antigen, the variable regions can be "reshaped" or "humanized" by grafting CDRs derived from nonhuman antibody on the FRs present in the human antibody to be modified. Application of this approach to various antibodies has been reported by Sato, K., et al. *Cancer Res* (1993) 53:851–856. Riechmann, L., et al. *Nature* (1988) 332:323–327; Verhoeyen, M., et al. *Science* (1988) 239:1534–1536; Kettleborough, C. A., et al. *Protein Engineering* (1991) 4:773–3783; Maeda, H., et al. *Human Antibodies Hybridoma* (1991) 2:124–134; Gorman, S. D., et al. *Proc Natl Acad Sci USA* (1991) 88:4181–4185; Tempest, P. R., et al. *Bio/Technology* (1991) 9:266–271; Co, M. S., et al., *Proc Natl Acad Sci USA* (1991) 88:2869–2873; Carter, P., et al., *Proc Natl Acad Sci USA* (1992) 89:4285–4289; and Co, M. S. et al. *J Immunol* (1992) 148:1149–1154.

In general, these techniques involve identifying the regions responsible for binding and those responsible for supporting these binding domains and then grafting these CDRs onto human framework regions which support these binding regions. It will be evident that it is impossible simply to extrapolate this approach from one antibody raised against one antigen to the next. Antibodies with respect to a particular antigen will require carefully designed and particularly devised modifications to obtain the desired result.

Disclosure of the Invention

The invention provides antibodies immunoreactive with human IL-8 which are compatible with the human immune system so as to be less immunogenic to humans than the murine monoclonal antibodies presently available. The invention also provides intermediates for the preparation of these antibodies or their immunoreactive fragments. Thus, the invention provides proteins which comprise the variable regions of the heavy and light chains of antibodies which are immunospecific for human IL-8 wherein these variable regions have human characteristics. In general, these variable regions contain the complementarity determining regions (CDRs) of the pertinent antibody secreted by non-human cells but the framework regions (FRs) which characterize human antibodies.

By thus reshaping murine- or other nonhuman-derived immunoglobulins, their immunogenicity in human patients is minimized. Of course, these humanized forms, since they retain their immunospecificity, are useful in standard assay procedures for IL-8 and in IL-8 purification.

Thus, in one aspect, the invention is directed to a monoclonal antibody immunoreactive with human IL-8 wherein the framework regions (FRs) of the variable regions of said antibody and the constant regions of said antibody are compatible with the human immune system. More specifically, the invention is directed to a monoclonal antibody or immunoreactive fragment thereof, immunoreactive with human IL-8 and compatible with the human immune system, wherein the framework regions (FRs) of the variable regions of said antibody or fragment and any constant regions of said antibody or fragment are of human origin. The invention is also directed to intermediates in the preparation of these antibodies and to recombinant materials useful to produce the antibodies and their intermediates. The invention is also directed to methods to utilize these antibodies. The antibodies can be used therapeutically, diagnostically, and as reagents for purification of human or other IL-8.

MODES OF CARRYING OUT THE INVENTION

Figure 1:
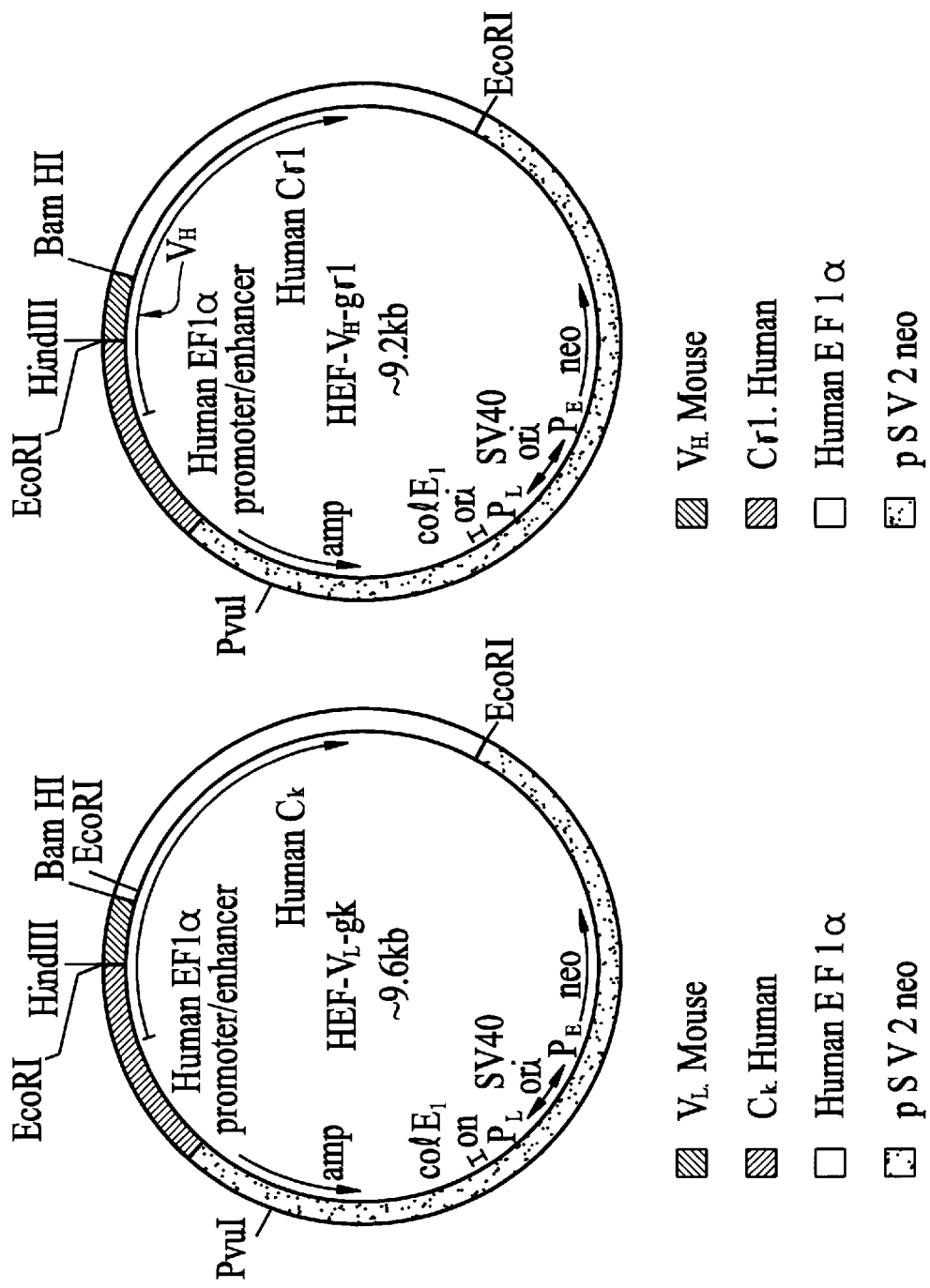
FIG. 1 represents expression plasmids HEF-VL-gκ and HEF-VH-gγ1 comprising a human elongation factor 1α (HEF-1α) promoter/enhancer system, useful for the expression of light chain and heavy chain of the present antibody, respectively.

The invention is directed to antibodies or fragments immunospecific for human IL-8 which have sufficient human characteristics so that their immunogenicity in human systems is lowered with respect to the corresponding antibodies derived from other species. Thus, the antibodies or immunoreactive fragments of the invention are compatible with the human immune system. By "compatible with the human immune system" is meant that the antibodies or fragments of the invention do not elicit a substantial immune response when administered to humans as compared to unmodified forms of nonhuman antibodies containing the same complementarity-determining regions (CDRs). Eliciting an immune response is clearly undesirable as antibodies raised against therapeutically administered materials undermine the effectiveness of the administered materials and in addition may provoke unwanted side-effects due to stimulation of the immune system per se. While the antibodies and fragments of the invention may not, of course, be completely neutral with respect to an immune response in a specific individual, their effect on the immune system of an individual will be substantially less than that elicited by corresponding nonhuman antibodies in their unmodified forms.

With respect to immunoreactive fragments, it is, of course, well known that immunospecificity may be retained using only the $F_{ab}$ or $F_{ab'}$, or $F_{(ab')_2}$ regions of immunoglobulins, since it is the variable regions represented by these fragments which are responsible for antigen specificity. The fragments can be obtained directly using recombinant or synthetic methods or may be obtained from the antibodies of the invention by known suitable cleavage techniques. An additional and particularly useful type of fragment is an $F_v$ fragment wherein the variable regions of the light and heavy chains are covalently linked through a peptide linker. Variable regions of this type are described by Bird, R. E. et al. *Trends in Biotechnology* (1991) 9:132–137 and by Huston, J. S. et al. *Proc Natl Acad Sci USA* (1988) 85:5879–5883. These regions can be linked head-to-tail so that the $F_v$ region can be recombinantly produced as a fusion protein.

One object of the invention is to provide a modified form of nonhuman antibodies which retain their immunospecificity with respect to human IL-8 but nevertheless are compatible with the human immune system by virtue of humanized reshaping of the nonantigen binding regions. It is recognized that various components of these antibodies, and various precursor forms are useful as intermediates in obtaining this desired result. The heavy- and light-chain portions of the antibodies could, in theory, be prepared separately and added together with optional subsequent formation of disulfide bonds or ligation with a synthetic linker. Similarly, individual portions of the heavy and light chains can be prepared separately and ligated to form complete sequences. Because of this possibility, these components are also subjects of the invention.

However, it is much more practical to prepare the antibodies or their fragments recombinantly using the nucleotide sequences encoding them placed in expression vectors and transfected or transformed into recombinant host cells. Thus, the expression systems for the heavy and light chains of the antibodies of the invention are also included within the scope of the invention, as are expression vectors for nucleotide sequences for portions of these chains. For antibodies or their fragments which are multimeric with separate chains linked through disulfide linkages, expression systems for the heavy and light chains or their variable regions may be disposed on a single vector, or separate vectors may be used for heavy and light chains. For construction of the single chain $F_v$ fragment, of course, a single vector contains the expression system for this single-chain form. In addition, isolated and purified or recombinant nucleotide sequences encoding the relevant portions of the desired heavy and light chains are included within the invention since these portions can be manipulated to obtain a nucleotide sequence encoding the entire chain.

Also included within the scope of the invention are nucleotide sequences encoding heavy or light chains which are themselves intermediates in the design and production of the monoclonal antibodies of the invention.

Thus, the invention includes the following proteins or peptides and polynucleotides containing nucleotide sequences encoding them: the individual CDR regions of nonhuman anti-IL-8 heavy and light chains preferably those of WS-4; variable regions of heavy and light chains containing human FRs and nonhuman CDRs immunoreactive with human IL-8; the foregoing variable regions linked together, e.g., through disulfide linkages; the foregoing variable regions linked to human constant regions and the antibodies formed by the resultant heavy and light chains; heavy and light chains containing nonhuman variable regions immunoreactive with human IL-8 and human constant regions and antibodies which are comprised of these heavy and light chains; and various chimeras of the foregoing, such as a heavy chain comprising a variable region with nonhuman CDRs and human FRs plus a human constant region coupled to a light chain containing a nonhuman variable region and a human constant region wherein the resultant antibody is immunospecific for human IL-8.

By "immunospecific for human IL-8" is meant that the antibody reacts with a human IL-8 to the substantive exclusion of other human proteins. It is understood that a certain amount of low-level cross-reactivity is expected, but the meaning of "immunospecific" is well understood in the art. Cross-reactivity may occur with respect to IL-8 of other species such as IL-8 obtained from rabbit. Furthermore, although frequently the discussion in the present application concerns "antibody" immunospecific for human IL-8, it is understood, based on the discussion above, that only a fragment of the antibody which contains the variable regions will be similarly effective. Therefore, unless otherwise evident from the context, "antibody" is intended to include immunoreactive fragments of the antibody, including single-chain versions thereof, such as the $F_v$ fragment discussed above.

Design of Chimeric Variable Regions

Examples 1 and 2 below describe in detail the recovery, cloning and sequencing of DNA encoding the variable region of heavy and light chains of WS-4 antibody. The variable region of the light chain is shown as positions 1–107 of SEQ ID NO 27 and that of heavy chain is shown as positions 1–122 of SEQ ID NO 29. As shown, the leader sequences are also included. The cloned mature variable light-chain region is a 107-amino acid protein; that for heavy chain is 122-amino acid protein. The amino acid positions are numbered in the sequence listing. The deduced amino acid sequences shown can be used to ascertain the location of the relevant CDRs since the basic structure of variable regions is understood. Thus, the location of these regions can be ascertained by analysis of the amino acid sequence as described by Kabat, E. A., et al. in "Sequences of Protein of Immunological Interest" US-DHHS (1991) and the later publications described in the background art section above. The four FRs largely adopt a β sheet conformation and the CDRs form loops connecting the FRs. The CDRs in some cases form part of the β sheet structure. The FRs form a scaffolding to hold the CDRs in close proximity to form the antigen-binding site. Example 3 below describes in detail the assignment of the CDR and FR regions in each chain. These are also presented in Tables 1 and 2 below. The amino acid sequences for each of these regions is there shown.

If desired, intermediate chimeric antibodies containing human constant regions and murine variable regions can be obtained as described in Example 4 hereinbelow to confirm that the correct variable regions have been obtained by showing successful binding of the resulting chimeric antibody to human IL-8.

The portions of the variable region which represent the framework regions (FRs) are then analyzed and compared to the corresponding FRs in human immunoglobulins of various subgroups. The subgroup is chosen which bears the highest homology to the murine FR region. In the case of the kappa light chain of WS-4, this is subgroup I; in the case of heavy chain of WS-4, subgroup III.

In general, as used in the present application, constant regions and framework regions "of human origin" refer to these regions of the immunoglobulin chains which are obtained by replacing amino acid residues found in the nonhuman antibodies with the corresponding residues at these positions found in human antibodies. In the case of constant regions, generally, the entire human constant region is substituted for that of the murine or other nonhuman antibody since this region is not germane to the immunospecificity of the antibody. For the framework regions, as described below, the human framework regions which correspond most closely in amino acid sequence to those found in the nonhuman antibody of interest are used as the basis for the substitution. However, straightforward one-for-one replacement of such human framework regions for the nonhuman ones is seldom possible; it is necessary to design specific replacement strategies which result in framework regions more closely resembling those of human origin than do the framework regions of the nonhuman immunoglobulin. This is illustrated, for example, in Table 2 where in FR3 restoring the phenylalanine at position 67 provided a better result than substituting a leucine as occurs in the model; similarly in FR2, substitutions at positions 41 and 47 were not favored with respect to the model human sequence. On the other hand, these positions contain residues characteristic of the human subgroup to which the model human sequence belongs.

In more detail, the variable regions from the WS-4 antibody were compared to all known human variable regions found in the National Biomedical Research Foundation (NBRF) database of protein sequences. The light-chain variable region of WS-4 was most similar to that of human antibody HAU (Watanabe, S. et al. Hoppe Seyler's *Z Physiolog Chem* (1990) 351:1291–1295) with a 69.2% identity; the heavy-chain variable region of WS-4 was most similar to that of human antibody VDH26 (Buluwela, L. et al. *EMBO J* (1988) 7:2003–2010) with 71.4% identity. The percent identities even to these human variable regions are less than those to other mouse variable regions, thus providing evidence that the variable regions of WS-4 "look like" mouse variable regions rather than human ones.

Comparison of the variable regions from WS-4 to consensus sequences for the subgroups of human variable regions as defined by Kabat, E. A. et al. 1991 (supra), specifically with respect to the FRs, are as follows: for the light chain, human subgroup I shows 64.4% identity with WS-4, while the remaining subgroups II–IV show only 51.3%, 57.3% and 57.5%, respectively. For the heavy-chain region, human subgroup III showed a 62.3% homology to WS-4 while the percentages for subgroups 1 and 2 were only 46.9% and 40.9%, respectively. These results are consistent with those obtained above since HAU belongs to human subgroup I and VDH26 to subgroup III.

An additional human antibody containing FRs very similar to those of WS-4 light chain is REI. There were only five different amino acid residues in the FRs of light-chain variable region of CAMPATH-1H as compared to original human REI (Palm, W. et al., Hoppe-Seyler's *Z. Physiol Chem* (1975) 356:167–191 and Epp, O. et al., *Biochemistry* (1975) 14:4943–4952); positions 39, 71, 104, 105, and 107 numbered according to Kabat et al., 1987; see Table 1. The two changes at positions 39 and 71 were changes back to the amino acids that occurred in the FRs of rat CAMPATH-1H light chain variable region (Riechmann, L. et al., *Nature* (1988) 332:323–327. The three changes in FR4 (positions 104, 105, and 107) were based on a J region from another human kappa light chain and, therefore, do not constitute a deviation from human.

Two versions of reshaped human WS-4 light-chain variable region were designed. In the first version (version "a"), the human FRs were identical to the REI-based FRs present in reshaped human CAMPATH-1H (Riechmann et al., 1988, supra) and the mouse CDRs were identical to the CDRs in mouse WS-4 light chain variable region. The second version (version "b") was based on version "a" with only one amino acid change at position 71 in human FR3. Residue 71 is part of the canonical structure for CDR1 of the light chain variable region as defined by Chothia C. et al., (*J Mol Biol* (1987) 196:901–917). The amino acid at this position is predicted to directly influence the structure of the CDR1 loop of the light chain variable region and, therefore, may well influence antigen binding ability. In the mouse WS-4 light chain variable region, position 71 is phenylalanine. In version "b" of reshaped human WS-4 light chain variable region, the phenylalanine at position 71 was changed to a tyrosine as found in mouse WS-4 light chain variable region. Table 1 shows the amino acid sequences of the mouse WS-4 light chain variable region, the FRs of REI as modified for use in reshaped human CAMPATH-1H antibody, and the two versions of reshaped human WS-4 light chain variable region.

TABLE 1

Design of Two Different Versions of Reshaped Human WS-4 Light Chain Variable Region

```
                 1              2                    3
        12345678901234567890123           45678901234
WS-4    DIQMTQSPASLSASVGETVTITC           RASEIIYSYLA
REI     DIQMTQSPSSLSASVGDRVTITC
RVLa    DIQMTQSPSSLSASVGDRVTITC           RASEIIYSYLA
RVLb    -----------------------           -----------
                FR1                             CDR1

4                    5
        567890123456789         0123456
WS-4    WYQQKQGKSPQLLVY         NAKTLAD
REI     WYQQKPGKAPKLLIY
RVLa    WYQQKPGKAPKLLIY         NAKTLAD
RVLb    ---------------         -------
              FR2                   CDR2

6         7         8                   9
        78901234567890123456789012345678         901234567
WS-4    GVSSRFSGSGSGTQFSLRISSLQPEDFGSYYC         QHHFGFPRT
REI     GVPSRFSGSGSGTDFTFTISSLQPEDIATYYC
RVLa    GVPSRFSGSGSGTDFTFTISSLQPEDIATYYC         QHHFGFPRT
RVLb    --------------Y-----------------         ---------
                      FR3                             CDR3

10
        8901234567
WS-4    FGGGTKLELK       pos 1-107 of SEQ ID NO 27
REI     FGQGTKVEIK
RVLa    FGQGTKVEIK       pos 1-107 OF SEQ ID NO 73
RVLb    ----------       pos 1-107 OF SEQ ID NO 77
          FR4
```

Note:
The FRs given for REI are those found in the reshaped human CAMPATH-1H antibody (Riechmann et al., 1988, supra). The five underlined amino acid residues in the REI FRs are those that differ from the amino acid sequence of human REI (Palm, W. et al., 1975, supra, Epp, O. et al., 1975, supra).

The FRs in the mouse WS-4 heavy chain variable region were most similar to the FRs in human heavy chain variable regions belonging to subgroup III. As discussed above, in comparing the mouse WS-4 heavy chain variable region to known human heavy chain variable regions, FR1, 2 and 3 were most similar to the human heavy chain variable region of VDH26 (Buluwela, L. et al., *EMBO J* (1988) 7:2003–2010), a member of subgroup III of human heavy chain variable regions. Since the sequence of FR4 of VDH26 is unknown, FR4 of 4B4 (Sanz, I. et al., *J Immunol* (1989) 142:883–887), also a member of subgroup III of human heavy chain variable regions, is used. For the construction of reshaped human WS-4 heavy chain variable region, these human heavy chain variable regions are used as a base for designing the reshaped human WS-4 heavy chain variable region.

Eight versions of reshaped human WS-4 heavy chain variable region were designed. In all eight versions, the human FRs were based on the FR1, 2 and 3 of VDH26 and FR4 of 4B4 and the mouse CDRs were identical to the CDRs in mouse WS-4 heavy chain variable region. Table 2 shows the amino acid sequences of mouse WS-4 heavy chain variable region, the FRs 1–3 of VDH26, the FR 4 of 4B4 and the eight versions of reshaped human WS-4 heavy chain variable region.

TABLE 2

Design of Reshaped Human WS-4 Heavy Chain Variable Region

```
                1          2          3
       12345678901234567890123456789012345
WS-4   EVKLVESGGGLIQPGDSLRLSCVTSGFTFS DYYLS
VDH26  EVQLLESGGGLVQPGGSLRLSCAASGFTFS
RVHa   EVQLLESGGGLVQPGGSLRLSCAASGFTFS DYYLS
RVHb   ------------------------------ -----
RVHc   ------------------------------ -----
RVHd   ------------------------------ -----
RVHe   ------------------------------ -----
RVHf   ------------------------------ -----
RVHg   ------------------------------ -----
RVHh   ------------------------------ -----
                   FR1                CDR1

4           5            6
       6789012345678  9 012ABC3456789012345
WS-4   WVRQPPGKALEWVG LIRNKANGYTREYSASVKG
VDH26  WVRQAQGKGLELVG
RVHa   WVRQAQGKGLELVG LIRNKANGYTREYSASVKG
RVHb   -----------W-- -------------------
RVHc   -----P-------- -------------------
RVHd   -----P-----W-- -------------------
RVHe   ----PP-----W-- -------------------
RVHf   -----P--A--W-- -------------------
RVHg   -----P-----W-- -------------------
RVHh   -----------W-- -------------------
            FR2            CDR2

7              8           9            100
       6789012345678901 2ABC345678901234 567890ABC12
WS-4   RFTISRDDSQSILYLQMNTLRGEDSATYYCAR ENYRYDVELAY
VDH26  RLTISREDSKNTLYLQMSSLKTEDLAVYYCAR
RVHa   RLTISREDSKNTLYLQMSSLKTEDLAVYYCAR ENYRYDVELAY
RVHb   -------------------------------- -----------
RVHc   -------------------------------- -----------
RVHd   -------------------------------- -----------
RVHe   -------------------------------- -----------
RVHf   -------------------------------- -----------
RVHg   -F------------------------------ -----------
RVHh   -F------------------------------ -----------
              FR3                           CDR3

110
       34567890123
WS-4   WGQGTLVTVSA
4B4    WGQGTLVTVSS
RVHa   WGQGTLVTVSS    pos 1-122 of SEQ ID NO 41
RVHb   -----------    pos 1-122 of SEQ ID NO 45
RVHc   -----------    pos 1-122 of SEQ ID NO 49
RVHd   -----------    pos 1-122 ot SEQ ID NO 51
RVHe   -----------    pos 1-122 of SEQ ID NO 55
RVHf   -----------    pos 1-122 of SEQ ID NO 59
RVHg   -----------    pos 1-122 of SEQ ID NO 63
RVHh   -----------    pos 1-122 of SEQ ID NO 65
         FR4
```

As shown above, Tables 1 and 2 indicate the various constructions that were made. The following considerations are also germane.

In the framing regions contained in the human heavy chain, we identified positions 1, 27, 28, 29, 30, 48 and 71 (numbered according to Kabat (supra) in Table 2) as having a possible adverse influence on antigen binding. Residue 1 is a surface residue located close to the CDR loops; residues 27–30 are predicted by Chothia, C. et al. *Nature* (1989) 342:877–883 as part of the canonical structure of CDR1. Chothia also predicts residue 71 to be part of the canonical structure of CDR2. The above seven positions were identical in both WS-4 and VDH26.

Residue 47 in this chain, located in FR2, is buried in the dimer of the light and heavy chains and supports the conformation of the binding sites according to Padlan, E. A. *Mol Immunol* (1991) 28:489–498. This residue is Leu in VDH26 and versions b, d, e, f, g and h of the reshaped human heavy chain contain Trp at this position. While this substitution appears to replace the human residue with that normally occurring in WS-4, this position is also Trp in the consensus sequences for human subgroup III and the region of the subgroup including this position is identical to that of WS-4. Thus, this replacement should not increase the immunogenicity of the antibody to humans. Residues 41 and 67 in VDH26 (in FR2 and FR3, respectively) are different from those found in WS-4, and also different from those of human subgroup III. The replacement at position 41 from Gln to Pro occurs in versions c-g and versions e and f have an additional replacement near residue 41 (see Table 2). In addition, versions g and h replace Leu at position 67 with Phe. These replacements, generally, restore the residues found in WS-4.

Construction of DNA Encoding Reshaped Human WS-4 Variable Regions, and Production of Antibodies The construction of DNA encoding reshaped human WS-4 variable regions is described in Example 5.

The first versions of DNA encoding reshaped human WS-4 light and heavy chain variable regions were synthesized, then sequenced to ensure that the entire DNA sequences of version "a" of reshaped human WS-4 light and heavy chain variable regions code for the correct amino acid sequence. Sequences of the reshaped human WS-4 antibody light chain variable region version "a" and heavy chain variable region version "a" are shown as the mature sequences in SEQ ID NO 73 and SEQ ID NO 41, respectively.

The other versions of the reshaped human WS-4 variable regions were constructed using slight modifications of published PCR-mutagenesis techniques (Kamman, M. et al., *Nucleic Acid Res* (1989) 17:5404). As described in the design of the reshaped human WS-4 variable regions, one additional version (version "b") of the reshaped human WS-4 light chain variable region was constructed and seven additional versions (versions "b", "c", "d", "e", "f", "g" and "h") of the reshaped human WS-4 heavy chain variable region were constructed. These additional versions contain a series of minor changes from the first versions. These minor changes in the amino acid sequences were achieved using PCR mutagenesis to make minor changes in the DNA sequences. PCR primers were designed that would introduce the necessary changes into the DNA sequence. Following a series of PCR reactions, each PCR product was cloned and sequenced to ensure that the changes in the DNA sequence had occurred as planned. The sequence of the reshaped human WS-4 antibody light chain variable region version "b" is shown as the mature protein region in SEQ ID NO 77. Sequences of the reshaped human WS-4 antibody heavy chain variable region versions "b", "c", "d", "e", "f", "g" and "h" are shown as the mature protein regions in SEQ ID NOs 45, 49, 51, 55, 59, 63 and 65, respectively.

Figure 7:
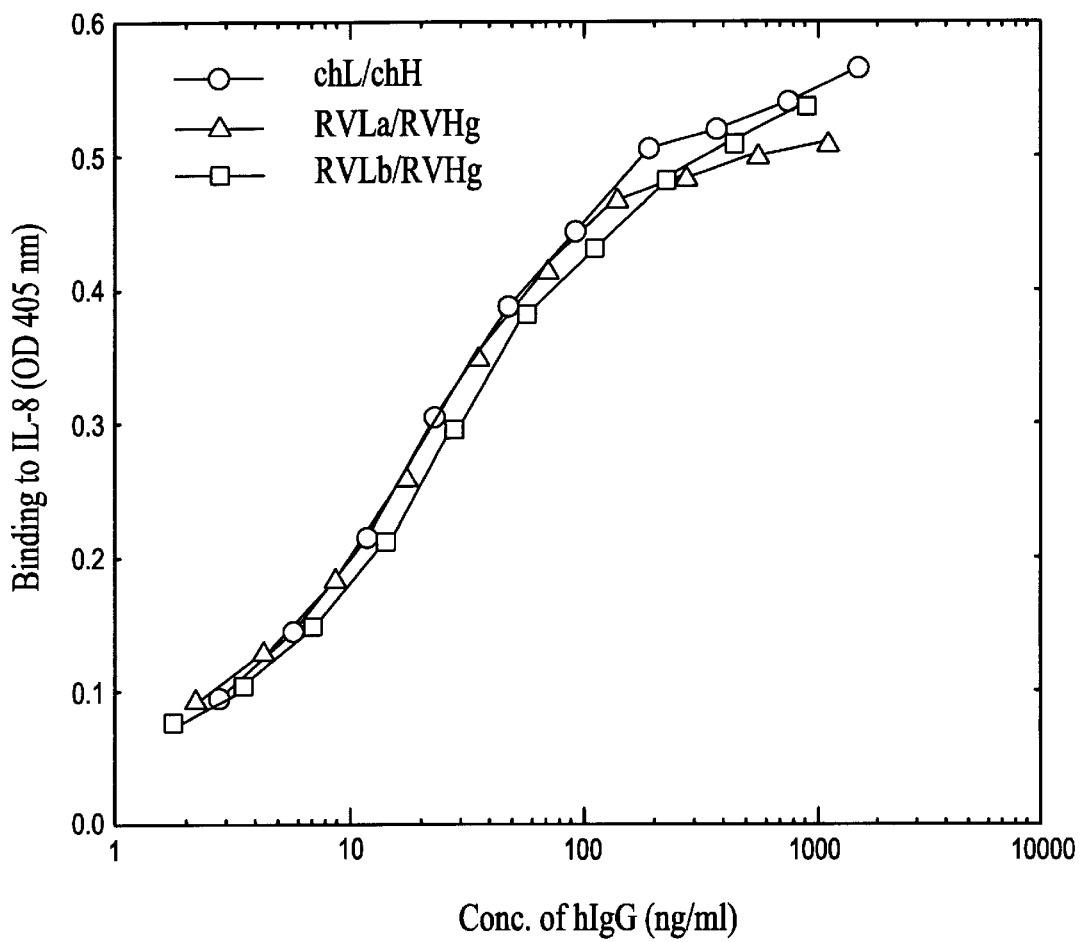
FIG. 7 is a graph showing a result of ELISA testing the ability to bind to human IL-8 of the purified chimeric (chL/chH) and reshaped (RVLa/RVHg and RVLb/RVHg) antibodies.
Figure 8:
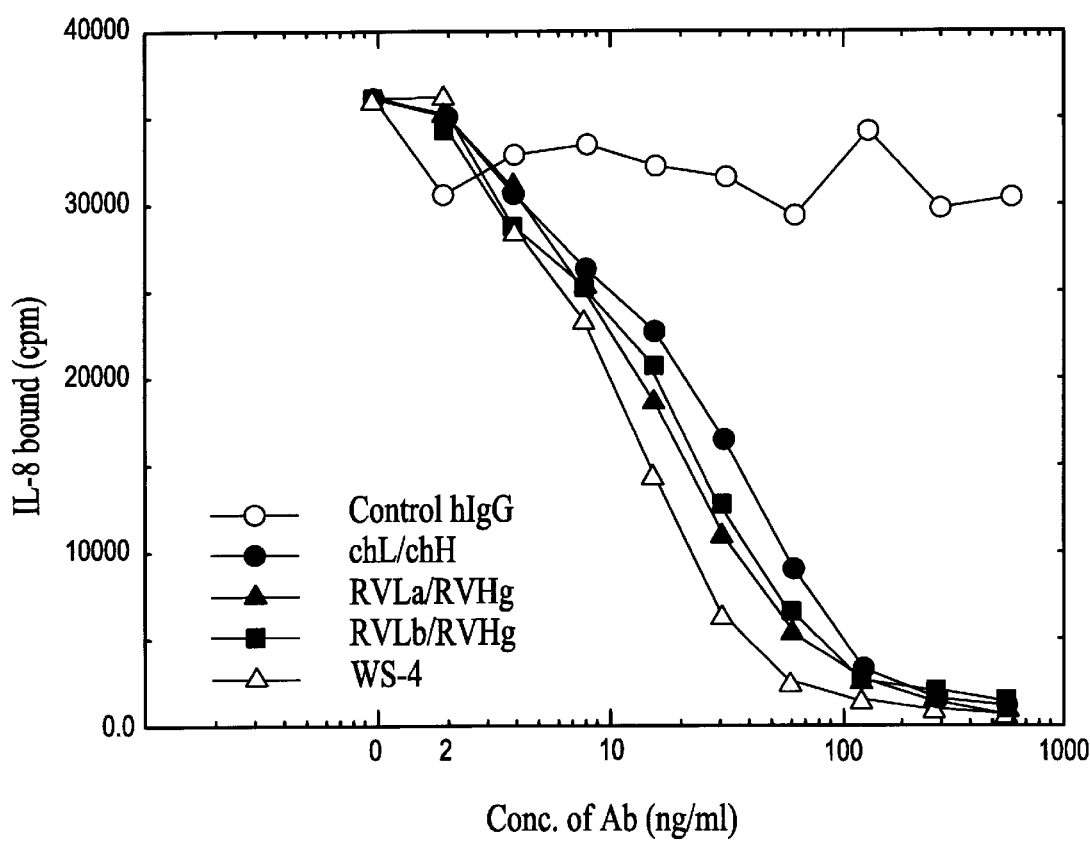
FIG. 8 is a graph showing the results of a receptor binding inhibition assay. This assay tests the ability of purified control human IgG, a chimeric antibody (chL/chH), reshaped antibodies (RVLa/RVHg and RVLb/RVHg) and the original WS-4 antibody to block binding of IL-8 to its receptor.

Once the DNA sequences of the different versions of reshaped human WS-4 variable regions were confirmed by sequencing, the reshaped human WS-4 variable regions were subcloned into mammalian cell expression vectors already containing human C regions. Reshaped human WS-4 light chain variable regions were joined to DNA sequences coding for human κ C region. Reshaped human WS-4 heavy chain variable regions were joined to DNA sequences coding for human γ-1 C region. Next, all combinations of the reshaped human light chain versions "a" and "b" with the heavy chain variable region versions "a" to "h" were tested for binding to human IL-8, and as a result, a reshaped human antibody comprising the light chain version "a" or "b" and the heavy chain version "g" exhibited an ability to bind to IL-8 at a same level as that of chimeric WS-4 (FIG. 7).

Alternatively, rather than ligating the DNA encoding the restructured variable regions to DNA encoding the relevant constant region, the variable regions can be coexpressed per se to obtain immunoreactive fragments. In still another alternative, the various coding sequences for the variable region of the heavy chain—i.e., RVH(a–h) of Table 1 and the DNA encoding the variable region of the light chain (i.e., sequences encoding RVL(a–b) of Table 2 can be amplified, isolated and ligated to a nucleotide sequence encoding a peptide linker of 12–19 amino acid residues. DNA encoding either the heavy- or light-chain variable region can constitute the upstream portion. The resulting construct encoding a fusion protein representing $F_v$ can be inserted into appropriate expression systems by conventional methods.

For the production of the present chimeric or reshaped human antibodies to human IL-8, any appropriate expression system, including eucaryotic cells, for example, animal cells, such as established mammalian cell lines, fungal cells, and yeast cells, as well as procaryotic cells, for example, bacterial cells such as *E. coli* cells, may be used. Preferably the present chimeric or reshaped human antibodies are expressed in mammalian cells such as COS cells or CHO cells. In such cases, a conventional promoter useful for expression in mammalian cells can be used. For example, a viral expression system including the human cytomegalovirus immediate early (HCMV) promoter is preferably used. Some examples of the expression vector containing the HCMV promoter are HCMV-VH-HCγ1, HCMV-VL-HCκ and the like derived from pSV2neo (WO92/19759).

Alternatively, other promoters suitable for gene expression of the present invention in mammalian cells can be used. These promoters include viral promoters such as retrovirus, polyoma virus, adenovirus and simian virus 40 (SV40) or mammalian cell-derived promoters such as human elongation factor 1α (HEF-1α) promoter. For example, SV40 or HEF-1α promoters are available according to the methods described by Mulligan, R. C. et al. (*Nature* (1979) 277:108– 114) or by Mizushima, S. et al. (*Nucleic Acids Res* (1990) 18:5322), respectively.

The example for the present invention is HEF-1α promoter. The human polypeptide chain elongation factor 1α (HEF-1α) is one of the most abundant proteins and expressed in most cells. The transcriptional activity of the human EF-1α promoter-enhancer is about 100-fold stronger than that of the SV40 early promoter-enhancer (D. W. Kim et al., *Gene* (1990) 91:217–223 and T. Uetsuki et al., *J Biol Chem* (1989) 264:5791–5798). The expression vectors containing HEF-1α promoter include HEF-VH-gγ1 and HEF-VL-gκ as shown in FIG. 1. As a replication origin, DNA sequences derived from polyoma virus, adenovirus, SV40 or bovine papilloma virus (BPV) are available. Additionally, in order to amplify the number of gene copies in the host cell, the aminoglucoside 3'-phosphotransferase gene, thymidine kinase (TK) gene, xanthine-guanine phosphoribosyltransferase (Ecogpt) gene and dihydrofolate reductase (dhfr) gene are available as selection markers.

In summary, the present invention first provides a light chain variable region and an heavy chain variable region of a nonhuman monoclonal antibody to human IL-8, as well as nucleotide sequences encoding them. These are useful for the construction of a human/nonhuman chimeric antibody and reshaped human antibody to human IL-8. The variable regions are derived from, for example, WS-4. This light chain variable region has an amino acid sequence shown in SEQ ID NO 27; and the heavy chain variable region has the amino acid sequence shown in SEQ ID NO 29. These amino acid sequences are natively encoded by nucleotide sequences shown in SEQ ID NOs: 26 and 28, respectively.

The present invention also relates to a chimeric antibody to human IL-8, comprising: (1) a light chain comprising a human light chain C region and a mouse light chain variable region; and (2) a heavy chain comprising a human heavy chain C region and a mouse heavy chain variable region. The mouse light chain variable region and the mouse heavy chain variable region and its encoding DNA are described above. The human light chain C region may be any human light chain C region, and for example, is human Cκ or Cλ. The human heavy chain C region may be any human heavy chain C region, and for example, is human Cγ1, γ2, γ3 or γ4.

For the production of the chimeric antibody, two expression vectors, i.e., one comprising a DNA coding for a mouse light chain variable region and a human light chain C region under the control of an expression regulatory region such as an enhancer/promoter system, and another comprising a DNA coding for a mouse heavy chain variable region and a human heavy chain C region under the expression regulatory region such as an enhancer/promoter system, are constructed. Next, the expression vectors are cotransfected into host cells such as mammalian cells, and the transfected cells are cultured in vitro or in vivo to produce a chimeric antibody. Alternatively, the nucleotide sequences encoding the heavy and light chains are introduced into a single expression vector, and the vector is used to transfect into host cells, which are then cultured in vivo or in vitro to produce a desired chimeric antibody.

The present invention further provides a reshaped antibody or fragments to human IL-8, comprising:

(A) a light chain comprising,
  (1) optionally, a human light chain C region, and
  (2) a light chain variable region comprising light chain FRs of human origin, and light chain CDRs of a nonhuman monoclonal antibody to human IL-8; and
(B) a heavy chain comprising,
  (1) optionally a human heavy chain C region, and
  (2) a heavy chain variable region comprising heavy chain FRs of human origin, and heavy chain CDRs of a nonhuman monoclonal antibody to human IL-8.

The reshaped antibody may be in conventional multimeric form or may be in a single-chain version, such as the $F_v$ fragment.

In a preferred embodiment, the light chain CDRs have amino acid sequences shown in SEQ ID NO 27 wherein the amino acid sequences of the CDRs are defined in Table 1; the heavy chain CDRs have amino acid sequences shown in SEQ ID NO 29 wherein the amino acid sequences of the CDRs are defined in Table 2; human light chain FRs are derived from the REI; human heavy chain FR1, 2 and 3 are derived from these of VDH26, and human heavy chain FR4 is derived from that of 4B4; the human light chain C region is human light chain C κ region; and the human heavy chain C region is human heavy chain C γ1 region.

In preferred embodiments, the light chain variable region has an amino acid sequence shown in Table 1 as RVLa or RVLb; and the heavy chain variable region has an amino acid sequence shown in Table 2 as RVHa, RVHb, RVHc, RVHd, RVHe, RVHf, RVHg or RVHh; with RVHg most preferable as the heavy chain variable region.

For the production of the reshaped human antibody, two kinds of expression vectors, i.e., one comprising a DNA encoding the reshaped light chain as defined above, under the control of an expression regulatory region, such as an enhancer/promoter system, and another comprising a DNA encoding the reshaped human heavy chain as defined above, under the expression control region, such as an enhancer/promoter system, are constructed. Next, the expression vectors are cotransfected into host cells such as mammalian cells, and the transfected cells are cultured in vitro or in vivo to produce a reshaped human antibody. Alternatively, a DNA encoding the reshaped human light chain and a DNA encoding the reshaped heavy chain are introduced into a single expression vector, and the vector is used to transfect into host cells, which are then cultured in vivo or in vitro to produce a desired reshaped human antibody.

The chimeric antibody and the reshaped human antibody thus produced can be isolated and purified with conventional processes, such as Protein A affinity chromatography, ion exchange chromatography, gel filtration and the like.

Utility

The present mouse light chain variable region, reshaped human light chain variable region, mouse heavy chain variable region and reshaped human heavy chain variable region are intrinsically regions which bind to human IL-8, and are therefore considered to be useful as such, or as fusion proteins with other proteins, for preparing pharmaceuticals or diagnostic agents.

Moreover, the present light chain variable region CDRs and heavy chain variable region CDRs are intrinsically regions which bind to human IL-8, and are therefore considered to be useful as such or as fusion proteins with other proteins, for preparing pharmaceuticals or diagnostic agents.

DNA encoding the mouse light chain variable region of the present invention is useful for construction of a DNA encoding a chimeric light chain or a DNA encoding a reshaped human light chain. Similarly, DNA encoding the heavy chain variable region of the present invention is useful for construction of a DNA encoding a chimeric heavy chain or a DNA encoding a reshaped human heavy chain. Moreover, DNA encoding light chain variable region CDRs of the present invention is useful for construction of a DNA encoding a reshaped human light chain variable region and a DNA encoding a reshaped human light chain. Similarly, DNA encoding heavy chain variable region CDRs of the present invention is useful for construction of a DNA encoding a reshaped human heavy chain variable region and a DNA encoding a reshaped human heavy chain. Additionally, $F_{(ab')_2}$, $F_{ab}$, $F_v$ and single chain $F_v$, wherein each $F_v$ of light chain and heavy chain are linked, can be produced in a suitable host cell, and then can be used for preparing pharmaceuticals or diagnostic agents.

The antibodies of the present invention are useful not only as therapeutic agents, but also as tools for purification of IL-8 and as reagents for immunoassays. For use as purification tools, the antibodies are employed in conventional procedures. In general, the antibody or an immunospecific fragment thereof will be used as an affinity ligand coupled to a solid support. A sample believed to contain IL-8 is placed in contact with the solid support. The support may be a chromatographic column, a derivatized plastic surface, or any adsorbent solid material. The IL-8 is allowed to bind to the immunospecific antibody or fragment coupled to solid support and unbound materials are removed. The IL-8 is then recovered from the solid support using standard procedures.

For use in immunoassays, the antibodies of the invention may be used in a variety of formats including direct or competitive assays for IL-8 with a variety of detection systems using well-known protocols generally known as RIAs, ELISAs, and the like. The antibodies can also be used as positive controls in assays for anti-IL-8 antibodies.

For example, for ELISA, appropriate plates are coated with antihuman IL-8 antibody, such as goat antihuman IL-8 polyclonal antibody. After blocking the plates, human IL-8 is added to wells. Following washing, purified sample or supernatant from antibody-producing cells containing the chimeric or reshaped antibody of the present invention is added. After incubation and washing, antihuman Ig antibody coupled to, for example, alkaline phosphatase, is added. After incubation and washing, enzyme substrate such as p-nitrophenyl phosphate is added and then after additional incubation the optical density at 405 nm is measured.

For use in therapy, e.g., to curtail neutrophil activation, after purification, evaluation and sterilization of the antibody, the chimeric or reshaped antibodies and fragments thereof may be administered by parenteral injection, for example, via intravenous, intramuscular, intraperitoneal, or subcutaneous injection, in a dosage range for humans of 1 to 1000 mg depending on the condition and age of the patient. This amounts to roughly 10 $\mu$g/kg-20 mg/kg of body weight for animals in general. Of course, optimization of dosage and of administration protocols for a particular species and for a particular subject are routine.

The antibody of the present invention and fragments thereof may be formulated in a conventional manner as described in *Remington's Pharmaceutical Science*, latest edition, Mack Publishing Company, Easton, Pa. For example, a preparation for injection may be obtained by the dissolving purified antibody in a solvent such as physiological saline or a buffer solution and then adding a substance such as Tween 80, gelatin or human serum albumin (HSA), to the solution to prevent nonspecific adsorption by the surfaces of the vessel containing the preparation. The preparation may be freeze-dried and reconstituted prior to use. Mannitol or glucose may be used as a filler for freeze-drying.

The present invention will be further illustrated by, but is by no means limited to, the following Examples.

Preparation A

Construction of Hybridoma WS-4

Starting hybridomas used in the present invention were constructed as follows. BALB/c mice were immunized with the recombinant human IL-8 produced in *E. coli*. Spleen cells from the mice were fused with P3X63-Ag8.653 mouse myeloma cells using a standard polyethylene glycol method. Monoclonal antibodies were screened for specific binding to human IL-8 by ELISA using 96-well microtiter plates coated with rhIL-8 (Ko, Y. C. et al., *J Immunol Methods* (1992) 149:227–235).

EXAMPLE 1

Cloning of DNA Encoding Variable Regions of Mouse Monoclonal Antibody to Human IL-8

1. Preparation of Total RNA

Total RNA from hybridoma WS-4 was prepared according to a standard guanidinium thiocyanate/cesium chloride method described by Chirgwin, J. M. et al., *Biochemistry* (1979) 18:5294–5299.

1×10⁷ cells of the hybridoma WS-4 were completely homogenized in 25 ml of 4 M guanidine thiocyanate (Fluka) solution. The homogenate was layered over a 5.7 M cesium chloride solution layer in a centrifuge tube, which was then centrifuged in a Beckman SW40 rotor at 31000 rpm at 20° C. for 14 hours to precipitate the RNA. The RNA precipitate was washed with 80% ethanol and dissolved in 200 µl of 20 mM Tris-HCl (pH 7.5) containing 10 mM EDTA and 0.5% sodium N-lauroylsarcosinate, and after adding Protenase (Boehringer) thereon to 0.5 mg/ml, incubated at 37° C. for 30 minutes in a water bath. The mixture was extracted with phenol and chloroform, and the RNA was precipitated with ethanol. Next, the RNA precipitate was dissolved in 200 µl of 10 mM Tris-HCl (pH 7.5) containing 1 mM EDTA.

2. Extraction of Messenger RNA (mRNA)

Next, poly A⁺ mRNA coding for mouse monoclonal antibody WS-4 heavy chain was purified from the total RNA using the FAST TRACK mRNA ISOLATION KIT version 3.2 (Invitrogen, USA) according to the manufacturer's instructions.

3. Synthesis of Single Stranded cDNA

Single stranded cDNA coding for mouse heavy chain variable region was synthesized from about 40 ng of the mRNA using the cDNA Cycle Kit (Invitrogen, USA) according to the manufacturer's instructions, then used for amplification of the cDNA in the same manner. Thereby single stranded cDNA coding for mouse light chain variable region was synthesized from about 10 µg of total RNA.

4. Amplification of cDNA Coding for Antibody variable Region by PCR Method (1) Amplification of cDNA coding for mouse heavy chain variable region The primers used for the PCR method were MHV (Mouse Heavy Variable) primers 1 to 12 represented in SEQ ID NOs: 13 to 24 and an MHC (Mouse Heavy Constant) primer represented in SEQ ID NO 25 (Jones, S. T. et al., Bio/Technology (1991) 9:88–89)

First, 100 µl of a PCR solution comprising 10 mM Tris-HCl (pH 8.3), 50 mM KCl, 0.1 mM dNTPs (DATP, dGTP, dCTP and dTTP), 1.5 mM MgCl₂, 0.001% (W/V) gelatin, 5 units of DNA polymerase Ampli Taq (Perkin Elmer Cetus), 0.25 µM of one of the MHV primers, 1.75 µM MHC primer and 1.5 µl of the reaction mixture of the single-stranded cDNA synthesis was prepared for each MHV primer, separately. Each PCR reaction mixture was covered with 50 µl of mineral oil, then heated at an initial temperature of 94° C. for 3 minutes, and then at 94° C. for 1 minute, 55° C. for 1 minute and 72° C. for 1 minute, in this order. After this temperature cycle was repeated 30 times, the reaction mixture was further incubated at 72° C. for 10 minutes.

(2) Amplification of cDNA coding for mouse light chain variable region

As primers for the PCR, MKV (Mouse Kappa Variable) primers 1 to 11 represented in SEQ ID NOs: 1 to 11 and an MKC (Mouse Kappa Constant) primer represented in SEQ ID NO 12 (Jones, S. T. et al., Bio/Technology (1991) 9:88–89) were used.

Amplification was carried out according to the same procedure as described for the amplification of the heavy chain variable region gene in section 4 (1) except that 0.25 µM of each MKV primer was mixed with 3 µM MKC primer and 2 µl of the reaction mixture of the single-stranded cDNA synthesis were used.

5. Purification and Digestion of PCR Products

The DNA fragments amplified by the PCR as described above were purified by agarose gel electrophoresis using a 1.5% low melting temperature agarose gel (Sigma). Each agarose piece containing DNA fragments of about 450 bp of heavy chain variable region or about 400 bp of light chain variable region in length was excised and melted at 65° C. for 5 minutes, and an equal volume of 20 mM Tris-HCl (pH 7.5) containing 2 mM EDTA and 200 mM NaCl was added thereon. The mixture was extracted with phenol and chloroform, and the DNA was recovered by ethanol precipitation. Next, the DNA precipitate was digested with 5 units of XmaI (New England Biolabs), in the buffer supplied with the enzyme (10 mM MgCl₂, 1 mM dithiothreitol, 10 mM Tris-HCl (Ph 7.9)) at 37° C. for 3 hours, and subsequently digested with 40 units of SalI (Takara Shuzou) in the buffer supplied with the enzyme, at 37° C. for 2 hours. The digestion mixture was extracted with phenol and chloroform, and the DNA was recovered by ethanol precipitation. The resulting DNA fragments were separated by agarose gel electrophoresis using low melting agarose (Sigma). Each agarose piece containing DNA fragments was excised and melted at 65° C. for 5 minutes, and an equal volume of 20 mM Tris-HCl (pH 7.5) containing 2 mM EDTA and 200 mM NaCl was added thereon. The mixture was extracted with phenol and chloroform, and the DNA fragment was recovered by ethanol precipitation and dissolved in 10 mM Tris-HCl (pH 7.5) containing 1 mM EDTA.

In this manner, a DNA fragment comprising a gene coding for a mouse κ light chain variable region, and a DNA fragment comprising a gene coding for a mouse heavy chain variable region were obtained. Both of the above DNA fragments had a SalI cohesive end at the 5'-end thereof and an XmaI cohesive end at the 3'-end thereof.

6. Ligation and Transformation

The SalI-XmaI DNA fragment comprising a gene coding for a mouse κ light chain variable region, prepared as described above, was ligated with a pUC19 vector (Takara Shuzou). The pUC19 vector was prepared by digesting plasmid pUC19 with XmaI, SalI, and diphosphorylating with E. coli C75 alkaline phosphatase (Takara Shuzou) in the buffer supplied with the enzyme. After extraction with phenol and chloroform, about 0.3 µg of the SalI-XmaI DNA fragment was ligated with about 0.1 µg of a pUC19 vector with 1 units of T4 DNA ligase (GIBCO BRL), at 16° C. for 4 hours.

Next, 5 µl of the above ligation mixture was added to 50 µl of competent cells of E. coli DH5α (GIBCO BRL), and the cells were incubated for 30 minutes on ice, for 1 minute at 42° C., and again for 1 minute on ice. After adding 400 µl of 2 X YT medium (Molecular Cloning: A Laboratory Manual, Sambrook et al., Cold Spring Habor Laboratory Press, 1989), the cell suspension was incubated at 37° C. for one hour, and inoculated onto an 2 X YT agar plate (Molecular Cloning: A Laboratory Manual, Sambrook et al., Cold Spring Habor Laboratory Press, 1989) containing 50 µg/ml ampicillin (Meiji confectionery), which was then incubated at 37° C. overnight to obtain E. coli transformants. Prior to the incubation, the surface of 2 X YT agar plate was covered with X-Gal (5-bromo-4 -chloro-3-indolyl-3-D-galactoside, Takara Shuzou) as a selection marker.

The transformant was cultured in 10 ml of 2 X YT medium containing 50 µg/ml ampicillin, at 37° C. overnight, and the plasmid DNA was prepared from the culture with a QIAGEN plasmid mini kit (QIAGEN) according to the manufacturer's instruction. The thus-obtained plasmid containing a gene coding for a mouse K light chain variable region derived from the hybridoma WS-4, was designated pUC-WS4-VL.

According to the same procedure as described above, except for using competent cells of E. coli JM109 (Nippon Gene), a plasmid containing a gene coding for a mouse heavy chain variable region derived from the hybridoma WS-4 was constructed from the SalI-XmaI DNA fragment, and designated pUC-WS4-VH.

EXAMPLE 2

Sequencing of DNA

Nucleotide sequences of a cDNA coding region in the above-mentioned plasmids were determined using an Automatic DNA sequencer 373A and Taq Dye Deoxy Terminator Cycle Sequence kit (Applied Biosystems) according to the manufacturer's instructions. The nucleotide sequences of the cDNA coding region in pUC-WS4-VL and pUC-WS4-VH are shown in SEQ ID NOs 26 and 28, respectively.

EXAMPLE 3

Determination of CDRs

The general structures of the light chain and heavy chain variable regions are similar to each other, wherein the 4 framework regions (FRs) are linked through 3 hypervariable regions, i.e., complementarity determining regions (CDRs). While amino acid sequences in the FRs are relatively well-conserved, amino acid sequences in CDRs are highly variable (Kabat, E. A. et al., "Sequences of Proteins of Immunological Interest", U.S. Dept. Health and Human Services 1991).

On the basis of the above-determined amino acid sequences of variable regions of mouse monoclonal antibodies to human IL-8, and according to Kabat, E. A. et al., "Sequences of Proteins of Immunological Interest", U.S. Dept. Health and Human Services 1991, CDRs of each variable region of mouse monoclonal antibodies to human IL-8 were determined as shown in Table 3.

TABLE 3

| Plasmid | SEQ ID NO | CDR1 | CDR2 | CDR3 |
|---------|-----------|------|------|------|
| pUC-WS4-VL | 27 | 24–34 | 50–56 | 89–97 |
| pUC-WS4-VH | 29 | 31–35 | 50–68 | 101–111 |

EXAMPLE 4

Confirmation of Expression of Cloned cDNA (Construction of Chimeric WS-4 Antibody)

1. Construction of Expression Plasmid

In order to construct expression vectors for chimeric WS-4 antibody, the cDNA clones pUC-WS4-VH and pUC-WS4-VL, coding for the mouse WS4 heavy chain variable region and light chain variable region, respectively, were modified by a PCR technique, and then introduced into the HEF expression vectors (referred to WO92/19759 and FIG. 1). Two sets of primers were designed and synthesized. A light chain variable region backward primer (SEQ ID NO 30) and heavy chain variable region backward primer (SEQ ID NO 31) were designed so that the primers hybridize with a DNA coding for the beginning of the leader sequence, maintain a DNA sequence essential for efficient translation (Kozak, M. et al. *J Mol Biol* (1987) 196:947–950) and form a HindIII cleavage site for cloning into the expression vector. A light chain variable region forward primer (SEQ ID NO 32) and a heavy chain variable region forward primer (SEQ ID NO 33) were designed so that the primers hybridize with a DNA coding for the terminal portion of the J region, maintain a DNA sequence essential for splicing into the C region and form a BamHI site for joining to the human C region in the expression vector.

Each 100 μl PCR mixture contained 20 mM Tris-HCl (pH 8.2), 10 mM KC1, 6 mM $(NH_4)_2SO_4$, 1% Triton X-100, 1.5 mM $MgCl_2$, 100 μM dNTPs, 2.5 U of Pfu DNA polymerase (STRATAGENE), 100 ng of a template DNA (pUC-WS4-VH or pUC-WS4-VL), 100 pmoles of each primer. Each PCR reaction mixture was covered with 50 μl of mineral oil, then heated at an initial temperature of 94° C. for 3 minutes, and then at 94° C. for 1 minute, 55° C. for 1 minute and 72° C. for 1 minute, in this order. After this temperature cycle was repeated 30 times, the reaction mixture was further incubated at 72° C. for 10 minutes.

Following PCR amplification, the PCR products were purified using 1.5% low melting agarose gel, digested with HindIII and BamHI, and introduced into the HEF expression vectors containing the human κ or γ1 chain C region DNA, and sequenced to confirm that errors were not introduced during the PCR amplification. The resulting expression vectors were designated as HEF-chWS4H-gγ1 and HEF-chWS4L-gκ.

2. Transient Expression in COS Cells

To observe transient expression of a chimeric WS-4 antibody, the expression vectors constructed as described above were tested in the COS cells. The vector DNAs, HEF-chWS4H-gγ1 and HEF-chWS4L-gκ, were cotransfected into COS cells by electroporation using a Gene Pulser apparatus (Bio Rad). Namely, COS cells were suspended in phosphate-buffered saline (PBS) to a cell concentration of $1×10^7$ cells/ml, and 10 μg (per each plasmid) of DNA was added to an 0.8 ml aliquot of the suspension. Pulses were applied at 1,500 V and 25 μF capacitance. After a recovery period of 10 minutes at room temperature, the electroporated cells were added to 15 ml of DMEM (GIBCO BRL) containing 5% γ-globulin-free fetal bovine serum (GIBCO BRL). After incubation for 96 hours, a culture supernatant was collected, centrifuged to eliminate cell debris, filtered with a 0.45 μm pore size disk filter (Gelman Science) and aseptically stored short-term at 4° C. or long-term at –20° C.

3. ELISA for Human IgG

The supernatant was first determined, by ELISA, if human-like antibody was produced by the transfected COS cells. By using known amounts of purified human IgG as a standard in this assay, it was also possible to estimate an amount of human-like antibody (in this case, chimeric WS-4 antibody chL/chH) present in the supernatant from the COS cells.

For this assay, 96-well multiplates (Nunc) were coated with 100 μl of 1 μg/ml goat antihuman IgG gamma chain antibody (2 μg/ml in 0.1 M sodium bicarbonate and 0.02% sodium azide) (TAGO). After blocking with dilution buffer (50 mM Tri-HCl (pH 7.2), 1% BSA, 1 mM $MgCl_2$, 0.15 M NaCl, 0.05% Tween 20 and 0.02% sodium azide), 100 μl of serially diluted supernatant was added to each well. After incubation and washing, 100 μl of 4000-fold diluted alkaline phosphatase-conjugated goat antihuman IgG gamma chain antibody (TAGO Inc, USA) was added to each well. After incubation and washing, 100 μl of 1 mg/ml p-nitrophenyl phosphate substrate solution (Sigma) was added. After incubation, the optical density at 405 nm was measured. Purified human IgG (Paesel+Lorei) was used as a standard.

The supernatant from the COS cells transfected with the vectors carrying the chimeric WS-4 genes was positive for the expression of a human-like antibody.

4. ELISA Assay for IL-8

Next, the same serially diluted supernatant from the COS cells transfected with the vectors carrying the chimeric WS-4 genes for chL/chH was assayed by ELISA for an ability to bind to human IL-8 to determine whether the produced antibody can bind to the antigen. For antigen-binding assay, 96-well multiplates (Nunc) were coated with 100 μl of goat antihuman IL-8 polyclonal antibody (R & D systems). Following blocking, 100 μl of recombinant human IL-8 (5 ng/ml, Amersham) was added to each well. After washing, 100 μl of the supernatant was added. After incubation and washing, 100 μl of 4000-fold diluted alkaline phosphatase-conjugated goat antihuman IgG gamma chain antibody (TAGO Inc, USA) was added to each well. After incubation and washing, 100 μl of 1 mg/ml p-nitrophenyl phosphate substrate solution (Sigma) was added. After incubation, the optical density at 405 nm was measured. There was no standard available for this assay.

Figure 2:
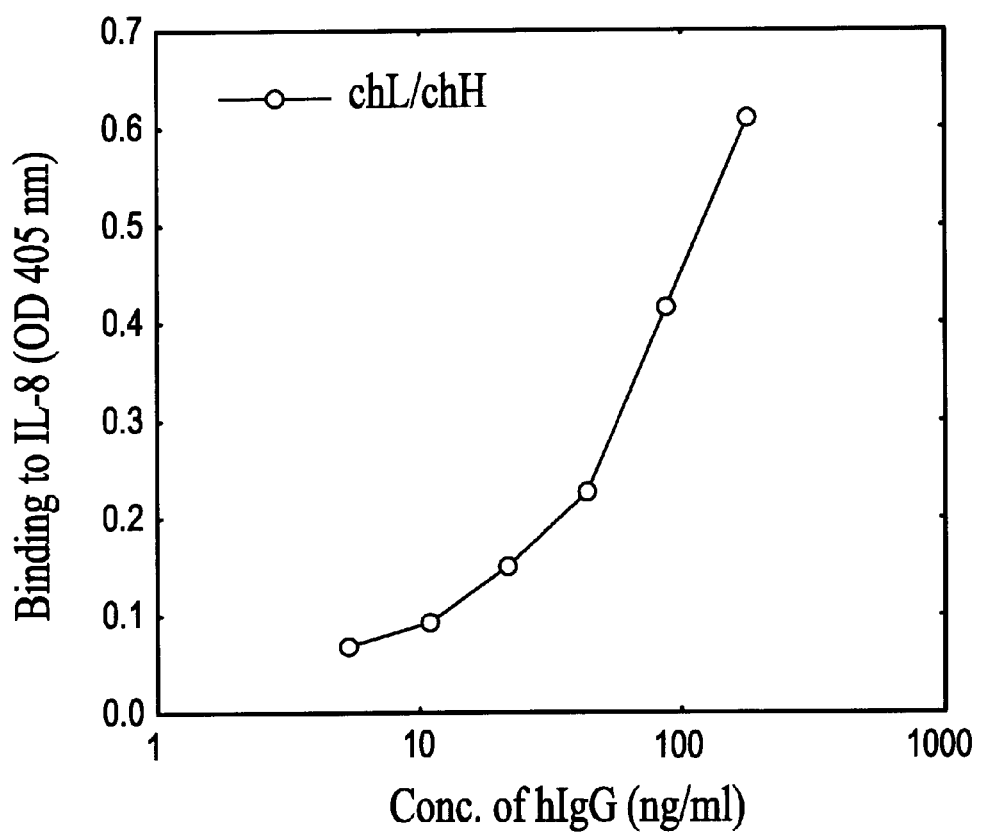
FIG. 2 is a graph showing a result of ELISA for confirmation of an ability to bind to human IL-8 of the chimeric WS-4 antibody (chL/chH) produced in the supernatant of COS cells.

A result is shown in FIG. 2. The culture supernatant samples exhibited a strong binding to IL-8, and the optical density at 405 nm was changed in a concentration-dependent manner, i.e., dependent on the monoclonal antibody concentration, as shown in FIG. 2, revealing the presence of an antibody to IL-8 in the sample, and suggesting that this chimeric WS-4 antibody has the correct structure of the mouse WS-4 monoclonal antibody variable region.

EXAMPLE 5

Construction of Reshaped Human WS-4 Antibody Heavy Chain Variable Region

The DNA coding for the first version of the reshaped human WS-4 heavy chain variable region was designed as follows. The DNA sequences for FR1, FR2 and FR3 of the VDH26 heavy chain variable region and FR4 of the 4B4 heavy chain variable region were linked to the DNA sequences for the CDRs of the mouse WS-4 heavy chain variable region. The DNA sequences which were similar to the consensus sequence for the splice donor site were mutated to minimize the possibility of aberrant splicing, and not to change the amino acid sequence. A HindIII restriction site and Kozak consensus sequence were added to the 5' end and a BamHI restriction site and a splice donor sequence were added to the 3' end, so that the DNA fragment could be inserted into HEF expression vector. Then the DNA sequence coding for the reshaped human WS-4 heavy chain variable region was divided into four oligonucleotides.

Figure 3A:
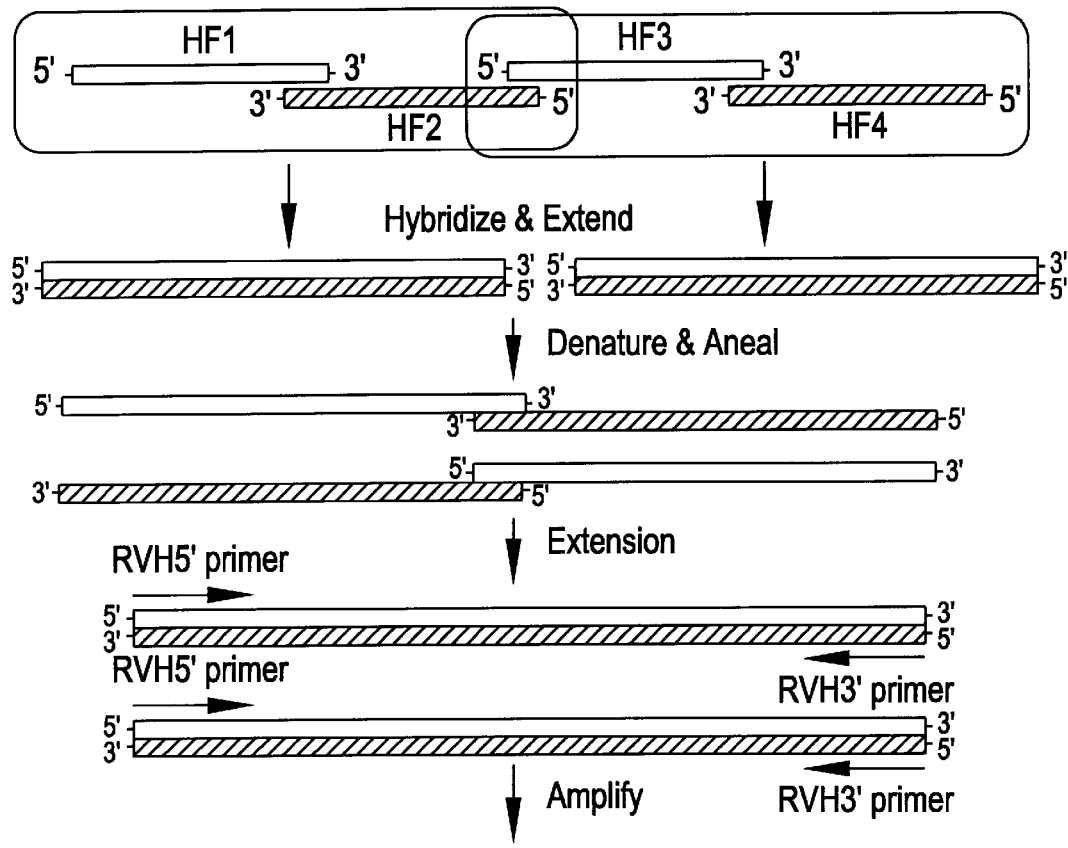
FIG. 3 is a diagram of the construction of the first versions of a reshaped human WS-4 heavy chain and light chain variable regions.
Figure 3B:
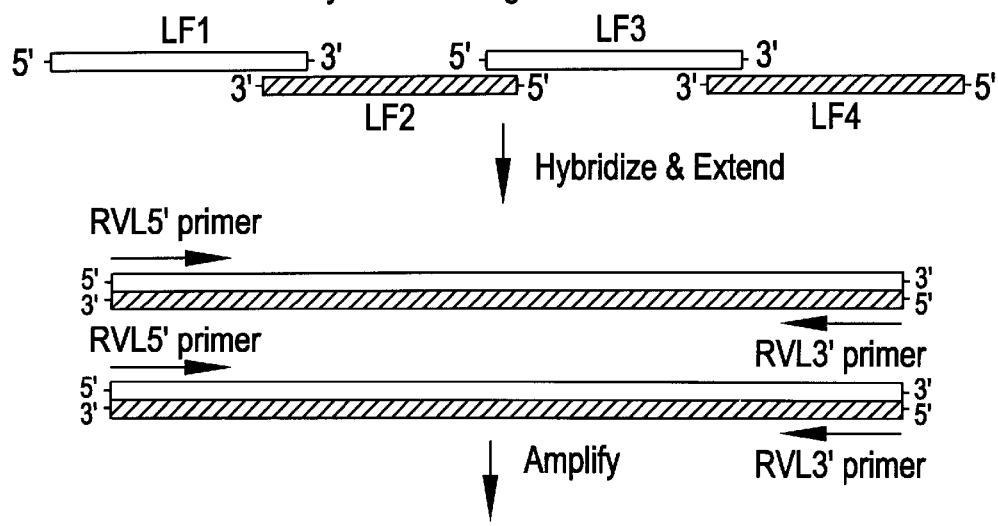
Figure 4:
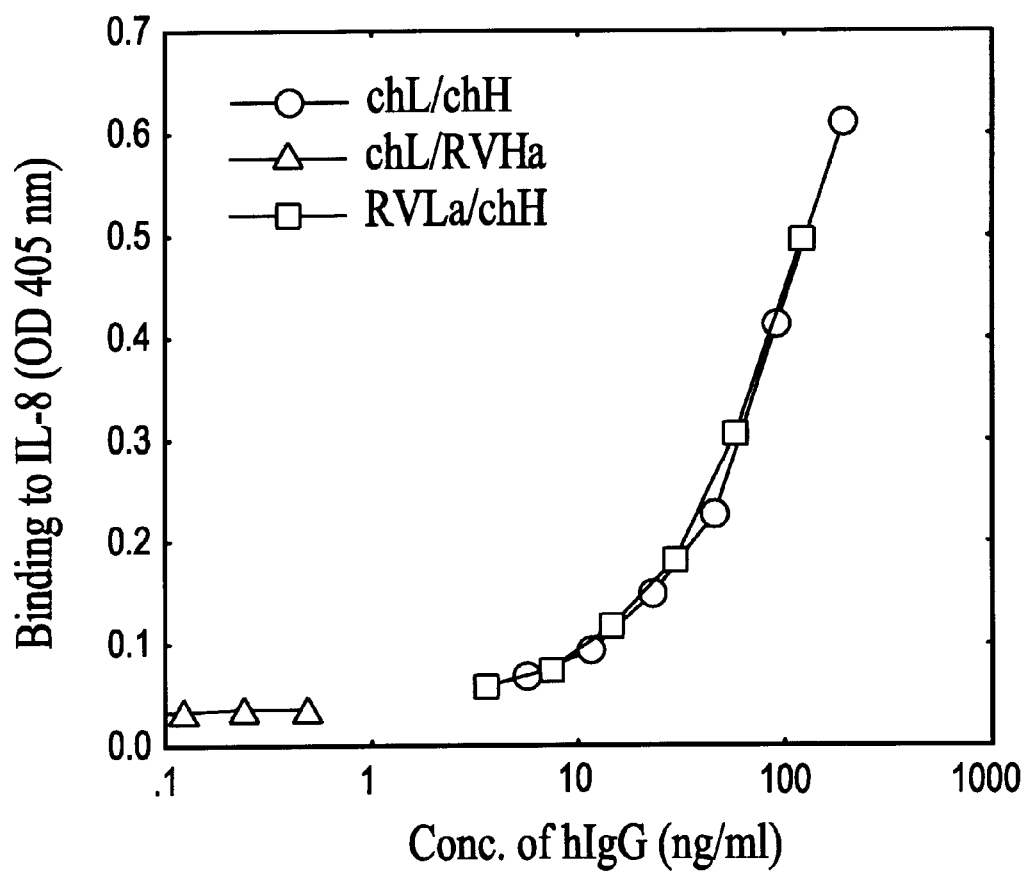
FIG. 4 is a graph showing a result of ELISA testing the ability to bind to human IL-8 of the reshaped light chain (RVLa) or heavy chain (RVHa). The antibodies chL/chH, RVLa/chH and chL/RVHa were produced in the supernatant of COS cells.
Figure 5:
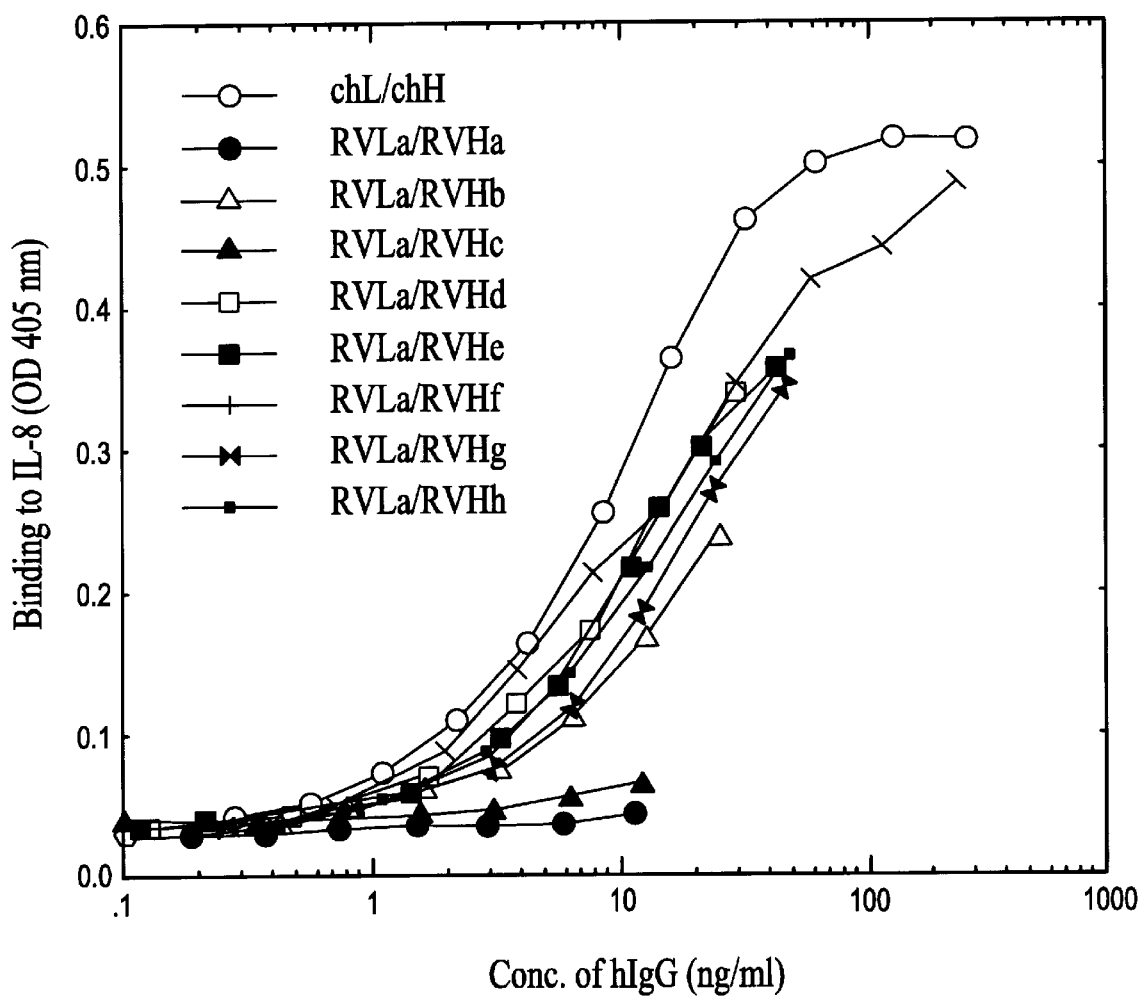
FIG. 5 is a graph showing a result of ELISA testing the ability to bind to human IL-8 of the reshaped antibodies comprising the first version "a" of light chain (RVLa) and various versions of heavy chain produced in the supernatant of COS cells.
Figure 6:
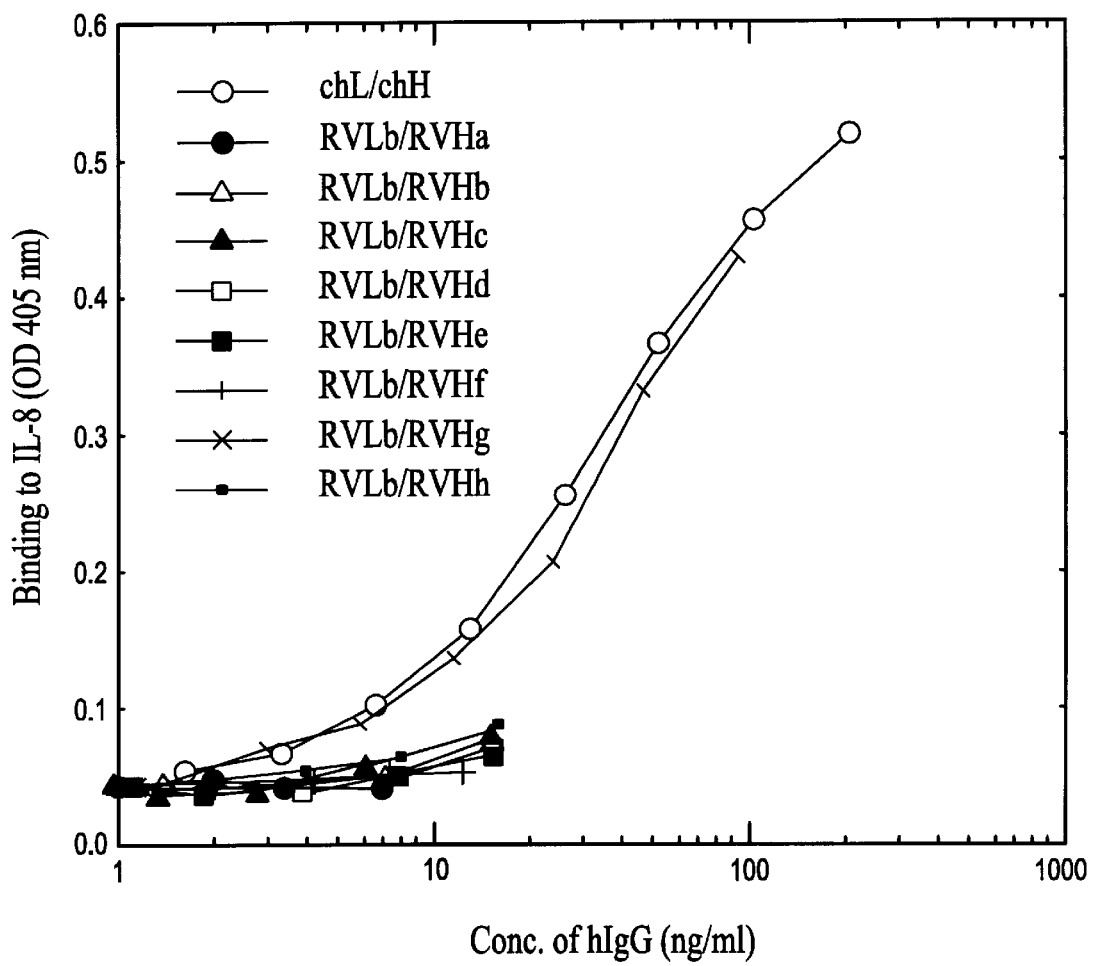
FIG. 6 is a graph showing a result of ELISA testing the ability to bind to human IL-8 of the reshaped antibodies comprising the second version "b" of light chain (RVLb) and various versions of heavy chain produced in the supernatant of COS cells.

The sequences of these oligonucleotides are shown in SEQ ID NOs; 34–37. These oligonucleotides are 113–143 bases in length and have overlapping regions with 20 bases in adjacent oligonucleotides. Among these oligonucleotides, HF1 (SEQ ID NO 34) and HF3 (SEQ ID NO 35) have sense DNA sequence and HF2 (SEQ ID NO 36) and HF4 (SEQ ID NO 37) have antisense DNA sequence. These oligonucleotides were synthesized with the automatic DNA synthesizer (381A, Applied Biosystems). The method for assembly of these oligonucleotides is described below. A process for construction of DNA coding for the first versions of reshaped human WS-4 antibody light chain variable region is shown in FIG. 3.

Namely, in the first PCR step, 98 μl PCR mixture contained about 100 ng each of HF1 and HF2, 2.5 U of Pfu DNA polymerase and the buffer supplied with the enzyme in a single tube. The other PCR mixture contained 2 pmoles each of HF3 and HF4 in another single tube. Each PCR tube was cycled, after denaturation at 94° C. for 3 min, at 94° C. for 2 min, 55° C. for 2 min and 72° C. for 2 min over 2 cycles, and then incubated at 72° C. for 10 min, thereby the two oligonucleotides were annealed and extended. The half volume from each reaction was mixed, and incubated under the same condition as described above, thereby the two extended oligonucleotides were annealed and further extended to obtain an entire oligonucleotide. In the second PCR step, 100 pmoles each of the external primers, RVH 5' primer (SEQ ID NO 38) and RVH3' primer (SEQ ID NO 39) were added to the first step PCR mixture. The PCR tube was overlaid with 50 μl of mineral oil and then cycled, after denaturation at 94° C. for 3 min, at 94° C. for 1 min, 55° C. for 1 min and 72° C. for 1 min over 45 cycles. The completion of the last cycle was followed by a final extension at 72° C. for 10 min.

Next, an approximately 450 bp DNA fragment was purified with 1.5% low melting agarose, digested with HindIII and BamHI, and then subcloned into the HEF-VH-gγ1 expression vector (FIG. 1). After DNA sequencing, a plasmid DNA encoding the correctly designed amino acid sequence was designated HEF-RVHa-gγ1. Both the DNA and deduced amino acid sequences coding for the heavy chain variable region in the expression vector HEF-RVHa-gγ1 are shown in SEQ ID NO 40.

The other versions of reshaped human WS-4 heavy chain variable region, "b", "c", "d", "e", "f", "g" and "h" were constructed by the following method.

The second version "b" (RVHb) was constructed using a PCR-based mutagenesis. The mutagenic primers, LTW-1 (SEQ ID NO 42) and LTW-2 (SEQ ID NO 43), designed to change the nucleotide T to G at position 197, resulted in the amino acid change of Leu to Trp at position 47 (determined by Kabat, E. A) in the FR2. The plasmid HEF-RVHa-gγ1 was used as the template DNA. The final PCR product was purified, digested with HindIII and BamHI, and then cloned into the HEF expression vector to yield the plasmid, HEF-RVHb-gγ1. Both the DNA and deduced amino acid sequences coding for the heavy chain variable region in the expression vector HEF-RVHb-gγ1 are shown in SEQ ID NO 44.

The third version "c" (RVHc) and the fourth version "d" (RVHd) were also constructed using a PCR-based mutagenesis. The mutagenic primers, QTP-1 (SEQ ID NO 46) and QTP-2 (SEQ ID NO 47), were designed to change the nucleotide A to C at position 179, resulted in the amino acid change of Gln to Pro at position 41 in the FR2. The plasmids HEF-RVHa-gγ1 and HEF-RVHb-gγ1 were used as the template DNA for version "c" and "d", respectively. The final PCR products were purified, digested with HindIII and BamHI, and then cloned into the HEF expression vector to yield the plasmids, HEF-RVHc-gγ1 and HEF-RVHd-gγ1. Both the DNA and deduced amino acid sequences coding for heavy chain variable region in the expression vector HEF-RVHc-gγ1 and HEF-RVHd-gγ1 are shown in SEQ ID NO 48 and 50, respectively.

The version "e" (RVHe) was constructed using the mutagenic primers, ATP-1 (SEQ ID NO 52) and ATP-2

(SEQ ID NO 53), designed to change the nucleotide G to C at position 175, resulting in the amino acid change of Ala to Pro at position 40 in the FR2. The plasmids HEF-RVHd-gγ1 was used as the template DNA for version "e". Thus the HEF expression vector HEF-RVHe-gγ1 was constructed. Both the DNA and deduced amino acid sequences coding for heavy chain variable region in the expression vector HEF-RVHe-gγ1 are shown in SEQ ID NO 54.

The version "f" (RVHf) was constructed using the mutagenic primers, GTA-1 (SEQ ID NO 56) and GTA-2 (SEQ ID NO 57) designed to change the nucleotide G to C at position 188, resulting in the amino acid change of Gly to Ala at position 44 in the FR2. The plasmids HEF-RVHd-gγ1 was used as the template DNA for version "f". Thus the HEF expression vector HEF-RVHf-gγ1 was constructed. Both the DNA and deduced amino acid sequences coding for the heavy chain variable region in the expression vector HEF-RVHf-gγ1 are shown in SEQ ID NO 58.

The version "g" and "h" (RVHg and RVHf, respectively) were constructed using the mutagenic primers, LTF-1 (SEQ ID NO 60) and LTF-2 (SEQ ID NO 61), designed to change the nucleotide C to T at position 265, resulting in the amino acid change of Leu to Phe at position 70 in the FR3. The plasmids HEF-RVHd-gγ1 and HEF-RVHb-gγ1 were used as the templates DNA for version "g" and "h", respectively. Thus the HEF expression vectors HEF-RVHg-gγ1 and HEF-RVHh-gγ1 were constructed. Both the DNA and deduced amino acid sequences coding for heavy chain variable region in the expression vector HEF-RVHg-gγ1 and HEF-RVHh-gγ1 are shown in SEQ ID NO 62 and 63, respectively.

Construction of Reshaped Human WS-4 light chain variable region

For the design of the reshaped human WS-4 VL region, the DNA sequences for the FRs present in the REI-based reshaped human PM-1 VL region (Sato et al., 1993) were joined with the DNA sequences for the CDRs of the mouse WS4 VL region. Then a HindIII restriction site and a Kozak consensus sequence were added to the 5' end and a BamHI restriction site and a splice donor sequence were added to the 3' end of the above DNA sequence. Then the DNA sequence coding for the reshaped human WS-4 light chain variable region was divided into four oligonucleotides.

The sequences of these oligonucleotides are shown in SEQ ID NOs 66–69. The DNA sequence was divided into four oligonucleotides which were 106–124 bases in length and had an overlapping regions of 19 or 23 bases. Among these four oligonucleotides, LF1 (SEQ ID NO 66) and LF3 (SEQ ID NO 68) have sense DNA sequence and LF2 (SEQ ID NO 67) and LF4 (SEQ ID NO 69) have antisense DNA sequence. These oligonucleotides were synthesized and assembled by the same PCR method described in the construction of the reshaped human WS-4 heavy chain variable region, except that RVL5'primer (SEQ ID NO 70) and RVL3'primer (SEQ ID NO 71) were used as external primers for amplification.

After the PCR reaction, a DNA fragment of approximately 400 nucleotides was purified using a 1.5% low melting agarose gel, digested with HindIII and BamHI, and subcloned into an identically digested pUC vector. After DNA sequencing, the HindIII-BamHI fragment encoding the correctly designed amino acid sequence was excised from the pUC plasmid DNA and introduced into the HEF expression vector, yielding HEF-RVLa-gκ. Both the DNA and deduced amino acid sequences coding for the light chain variable region in the expression vector HEF-RVLa-gκ are shown in SEQ ID NO 72.

The second version "b" (RVLb) was constructed using the mutagenic primers, FTY-1 (SEQ ID NO 73) and FTY-2 (SEQ ID NO 74), designed to change the nucleotide T to A at position 269, resulting in the amino acid change of Phe to Tyr at position 71 in the FR3. The plasmids HEF-RVLa-gκ was used as the template DNA for version "b". Thus the HEF expression vector HEF-RVLb-gκ was constructed. Both the DNA and deduced amino acid sequences coding for the light chain variable region in the expression vector HEF-RVLb-gκ are shown in SEQ ID NO 76.

EXAMPLE 6

Expression and Analysis of Different Versions of Reshaped Human WS-4 Antibody

For evaluation of the first versions of the reshaped human WS-4 antibody light chain (RVLa) and heavy chain (RVHa) constructed according to the method described above, each HEF-1α vector expressing reshaped human WS-4 light or heavy chains was cotransfected into COS cells with the HEF-1α vectors expressing chimeric WS-4 heavy or light chains, respectively. As a standard control, HEF-1α vectors expressing chimeric WS-4 light and heavy chains were also cotransfected into COS cells. The transfections of these vectors were achieved by electroporation using a Gene Pulser apparatus (Bio Rad). Briefly, COS cells were suspended in phosphate-buffered saline (PBS) to a cell concentration of $1 \times 10^7$ cells/ml, and to 0.8 ml aliquot of the suspension was added 10 μg (per each plasmid) of DNA. Pulses were applied at 1,500 V and 25 μF capacitance. After the recovery period of 10 minutes at room temperature, the electroporated cells were added to 15 ml of DMEM (GIBCO BRL) containing 5% γ-globulin-free fetal bovine serum. After incubation, a culture supernatant was collected, centrifuged, filtered and aseptically stored. The supernatant was analyzed by ELISA for: (1) the amount of human IgG antibody present in the supernatant and (2) the ability of that human IgG to bind to IL-8.

The evaluation of the first version "a" of the reshaped human WS-4 light chain variable region (RVLa) was conducted by cotransfecting its expression vector HEF-RVLa-gκ with the expression vector for chimeric WS-4 heavy chain (HEF-chWS4H-gγ1) to produce the antibody "RVLa/chH".

The evaluation of the first version "a" of the reshaped human WS-4 heavy chain variable region (RVHa) was conducted by cotransfecting its expression vector HEF-RVHa-gγ1 with the expression vector for chimeric WS-4 light chain (HEF-chWS4L-gκ) to produce the antibody "chL/RVHa". As a control, COS cells were also cotransfected with vectors expressing chimeric WS-4 light and heavy chains (HEF-chWS4L-gκ and HEF-chWS4H-gγ1, respectively) to produce the chimeric antibody "chL/chH". Data using unpurified COS cell supernatants showed that version "a" of the reshaped human WS-4 light chain (RVLa)

was equivalent to chimeric WS-4 light chain in assays for binding to IL-8. Version "a" of the reshaped human WS-4 heavy chain (RVHa), however, virtually abolished binding to IL-8 (FIG. 4). Because the version "a" of the reshaped human WS-4 heavy chain (RVHa) failed to bind to IL-8, other versions were constructed according to the method described above.

For the version "a", chimeric WS-4 light chain and RVLa were used for evaluating the reshaped human WS-4 heavy chain variable region versions "a" to "h". The evaluation for the eight versions of reshaped human WS-4 heavy chain variable regions was conducted by cotransfecting each vector expressing reshaped human WS-4 heavy chain (HEF-RVHa-gγ1, HEF-RVHb-gγ1, HEF-RVHc-gγ1, HEF-RVHd-gγ1, HEF-RVHe-gγ1, HEF-RVHf-gγ1, HEF-RVHg-gγ1 or HEF-RVHh-gγ1) with the vector expressing the version "a" of the reshaped human WS-4 light chain (HEF-RVLa-gκ) to produce reshaped human antibodies (RVLa/RVHa, RVLa/RVHb, RVLa/RVHc, RVLa/RVHd, RVLa/RVHe, RVLa/RVHf, RVLa/RVHg and RVLa/RVHh). Cells were also cotransfected with vectors expressing chimeric WS-4 light and heavy chains (HEF-chWS4L-gκ and HEF-chWS4H-gγ1, respectively).

Data using unpurified COS cell supernatants showed that binding activities to IL-8 of the reshaped human antibodies RVLa/RVHb, RVLa/RVHd, RVLa/RVHe, RVLa/RVHf, RVLa/RVHg and RVLa/RVHh were comparable to that of the chimeric antibody chL/chH. With regard to the production of antibody, RVLa/RVHg was produced most efficiently among these antibodies. Consequently, the pairing of version "a" of reshaped human WS-4 light chain and version "g" of the reshaped human WS-4 heavy chain was equivalent to the chimeric WS-4 antibody (chL/chH) both in binding to IL-8 and in production (FIG. 5).

Next, the evaluation of the second version "b" of the reshaped human WS-4 light chain variable region (RVLb) was conducted by cotransfecting of its expression vector HEF-RVLb-gκ with each expression vector to produce the reshaped human WS-4 heavy chain as described above. Data using unpurified COS cell supernatants showed that only pairing of version "b" of the reshaped human WS-4 light chain and version "g" of the reshaped human WS-4 heavy chain was equivalent to chimeric WS-4 antibody (chL/chH) both in binding to IL-8 and in production thereof (FIG. 6).

To confirm these data, chimeric and reshaped human WS-4 antibodies were concentrated and purified from COS cell supernatants using Protein A. Namely the culture media from COS cells was concentrated using a 30 kd cut-off ultrafiltration device (Amicon). The concentrated media was purified using Protein A agarose (Affi-Gel Protein A MAPSII kit, BioRad). Briefly, the concentrated media was applied to a Protein A agarose column that was equilibrated with five bed volumes of binding buffer. The column was washed with 15 bed volumes of the binding buffer, followed by 5 bed volumes of the elution buffer. The eluate was concentrated and the buffer changed to PBS using a microconcentrator (Centricon 30, Amicon). The purified antibodies were used for further analysis.

The analysis of purified samples of chimeric WS-4 antibody, and reshaped human WS-4 antibodies with versions "a" or "b" of the light chain variable region and version "g" of the reshaped human heavy chain variable region, RVLa/RVHg and RVLb/RVHg, was carried out. The binding of each of the reshaped human antibodies RVLa/RVHg and RVLb/RVHg to IL-8 is equivalent to the chimeric WS-4 antibody (FIG. 7).

EXAMPLE 7

Neutralizing Activity

The neutralizing activity of the various forms of humanized anti-IL-8 antibody can be assessed in the assays described below for inhibition of IL-8 receptor binding or inhibition of IL-8-mediated chemotaxis. Both assays utilize neutrophils. The neutrophils were prepared as follows: About 100 ml of heparinized venous blood was layered onto a Mono-Poly resolving solution (ICN) and centrifuged according to the manufacturer's instructions. The neutrophil layer was harvested and washed with RPMI-1640 medium containing 1% BSA. Contaminating red blood cells were lysed by addition of 150 mM ammonium chloride. The suspension was centrifuged and the pellet containing neutrophils was washed and resuspended at the desired cell density ($2\times10^7$ cells/ml) in RPMI-1640 medium containing 1% BSA. Neutrophils constituted more than 95% of the suspended cells as determined by the Cytospin assay (Shandon) and by the Diff-Quik staining method (Green Cross Corp.).

For the receptor binding inhibition assay, the neutrophil suspension was centrifuged and resuspended at a concentration of $2\times10^7$ cells/ml in binding buffer (D-PBS containing 1% BSA and 0.1% sodium azide). In order to block $F_c$ receptors on the neutrophils, another chimeric antibody, SK-2 (PCT application PCT/JP94/00859), was added to a final concentration of 50 μg/ml and IL-6 was added to a final concentration of 40 ng/ml. The resulting mixture was incubated on ice for 30 min. The chimeric SK-2 antibody has the same $F_c$ region as the humanized antibody of the present invention and binds human IL-6 forming an immune complex.

Then, $^{125}$I-labeled IL-8 (74 TBq/nM; Amersham) was admixed with unlabeled IL-8 (Amersham) at an optimal final concentration of 4 ng/ml in binding buffer. WS-4 mouse antibody, chimeric antibody or reshaped human antibodies were serially diluted into the binding buffer. Then 50 μl each of the IL-8 solution and the antibody solution were mixed and preincubated on ice for 30 min. After the preincubation, 100 μl of the neutrophil suspension were added and additionally incubated on ice for 1 hr, with agitation every 15 min. Following the incubation, the cell suspension is layered onto a 200 μl, 20% sucrose cushion, centrifuged and frozen. The frozen cell pellets were then cut, and the radioactivity therein was counted using a γ-counter (Aloka) to measure the cell-associated radiolabeled ligand. The results are shown in FIG. 8.

FIG. 8 shows that the inhibition that results from ligand/receptor binding of a transiently-produced chimeric antibody (chL/chH) and by reshaped human antibodies (RVLa/RVHg and RVLb/RVHg) was equivalent to the mouse WS-4 antibody.

The chemotaxis inhibition assay is conducted in a multi-well chemotaxis chamber containing a lower and upper compartment and polycarbonate frame filter with a pore size of 5 μm (NeuroProbe Inc.). WS-4 mouse antibody, chimeric antibody or reshaped human antibodies are serially diluted, and admixed with 20 ng/ml human IL-8 (Amersham) in RPMI-1640 medium containing 1% BSA. Then, 36 μl of this admixture is aliquoted into the wells in the lower compartment of the chemotaxis chamber and a frame filter is placed on top of the lower compartment. The entire chamber is preincubated at 37° C. for 30 min, and then 100 μl of a neutrophil suspension is added to each well in the upper compartment. The chamber is additionally incubated at 37° C. for 1 hr. Neutrophils which migrate and adhere to the membrane are fixed with methanol and stained with Giemsa stain or with Diff-Quik stain (Green Cross Corp.) according to the manufacturer's instructions. Then the absorbance of the sample at 540 nm wave length is measured in a Microplate Reader Model 3350 (BioRad), or the cells are directly observed and counted using a light microscope. Alternatively, neutrophils which migrate and adhere to the membrane are fixed with methanol and stained with mouse antihuman neutrophil antibody (BioMakor™bm) as a primary antibody and FITC (fluorescein isothiocyanate)-conjugated antimouse IgG antibody (BioMakor™bm) as a secondary antibody according to the manufacturer's instructions. The fluorescein intensity is then measured in a Leitz PATIMED MPV-MT2 machine (Leica). In all of the above procedures for measuring chemotaxis, the chemotactic index is defined as the ratio of the intensity, absorbance, or direct cell count representing the number of cells which migrate and adhere to the membrane in the absence of IL-8, to those cells which migrate and adhere to the membrane in the presence of IL-8.

Industrial Applicability

The present invention provides a reshaped human antibody to human IL-8, comprising a human antibody wherein the CDRs of the human variable regions are replaced by the CDRs of mouse monoclonal antibody immunoreactive with human IL-8. Since a major portion of the reshaped antibody is derived from human immunoglobulin sequences, the present reshaped human antibody is less immunogenic in humans than antibodies raised in nonhuman subjects, and is therefore promising for therapeutic uses in humans.

Reference to Deposited Microorganisms under Rule 13-2 of Budapest Treaty:

| Identification of Microorganism | Deposition Number | Deposition Date |
| --- | --- | --- |
| E. coli DH5α (HEF-chWS4L-gκ) | FERM BP 4739 | July 12, 1994 |
| E. coli JM109 (HEF-chWS4H-gγ1) | FERM BP 4740 | July 12, 1994 |
| E. coli DH5α (HEF-RVLa-gκ) | FERM BP 4738 | July 12, 1994 |
| E. coli JM109 (HEF-RVHg-gγ1) | FERM BP 4741 | July 12, 1994 |

All of the deposited microorganisms have been deposited at the National Institute of Bioscience and Human Technology Agency of Industrial Science and Technology, 1–3, Higashi 1-chome, Tsukuba-Shi, Ibaraki, Japan 305.

We claim:

1. A polynucleotide which comprises coding regions comprising a nucleotide sequence encoding a reshaped antibody or a fragment of said antibody that specifically binds IL-8, wherein said reshaped antibody comprises the amino acid sequence of SEQ ID NO: 73 (RVLa) or SEQ ID NO: 77 (RVLb) as a V region of an L chain and SEQ ID NO: 63 (RVHg) as a V region of an H chain.

2. The polynucleotide of claim 1 wherein said fragment is $F_{ab}$, $F_{ab'}$, or $F_{(ab')_2}$ or single chain $F_v$.

3. The polynucleotide of claim 1 wherein said coding regions further comprise a nucleotide sequence encoding a C region of an L chain and a C region of an H chain of a human antibody.

4. The polynucleotide of claim 3 wherein said coding regions are operably linked to control sequences which effect their expression.

5. A recombinant host cell which contains the polynucleotide of claim 4.

6. A method to produce a reshaped antibody that specifically binds human IL-8 or a fragment of said antibody which comprises culturing the cells of claim 5 under conditions wherein said coding regions are expressed to produce said antibody or said fragment.

7. A polynucleotide which comprises coding regions comprising a nucleotide sequence encoding a variable (V) region of a light (L) chain of a reshaped antibody that specifically binds human IL-8 wherein the variable (V) region of the reshaped antibody comprises the amino acid sequence of SEQ ID NO: 73 (RVLa).

8. The polynucleotide of claim 7 wherein said coding regions further comprise a nucleotide sequence encoding a Constant (C) region of an L chain of a human antibody.

9. The polynucleotide of claim 7 wherein said coding regions are operably linked to control sequences which effect their expression.

10. The polynucleotide of claim 8 wherein said coding regions are operably linked to control sequences which effect their expression.

11. A recombinant host cell which contains the polynucleotide of claim 9.

12. A recombinant host cell which contains the polynucleotide of claim 10.

13. A method to produce a reshaped antibody that specifically binds human IL-8 or a fragment of said antibody which method comprises culturing the cells of claim 11 under conditions wherein said coding regions are expressed to produce said antibody or said fragment.

14. A method to produce a reshaped antibody that specifically binds human IL-8 or a fragment of said antibody which method comprises culturing the cells of claim 12 under conditions wherein said coding regions are expressed to produce said antibody or said fragment.

15. The method of claim 13 wherein said fragment is $F_{ab}$, $F_{ab'}$, $F_{(ab')2}$ or single chain $F_v$.

16. The method of claim 14 wherein said fragment is $F_{ab}$, $F_{ab'}$, $F_{(ab')2}$ or single chain $F_v$.

17. A polynucleotide which comprises coding regions comprising a nucleotide sequence encoding a V region of an L chain of a reshaped antibody that specifically binds human IL-8 wherein the variable (V) region of the reshaped antibody comprises the amino acid sequence of SEQ ID NO: 77 (RVLb).

18. The polynucleotide of claim 17 wherein said coding regions further comprise a nucleotide sequence encoding a C region of an L chain of a human antibody.

19. The polynucleotide of claim 17 wherein said coding regions are operably linked to control sequences which effect their expression.

20. The polynucleotide of claim 18 wherein said coding regions are operably linked to control sequences which effect their expression.

21. A recombinant host cell which contains the polynucleotide of claim 19.

22. A recombinant host cell which contains the polynucleotide of claim 20.

23. A method to produce a reshaped antibody that specifically binds human IL-8 or a fragment of said antibody which method comprises culturing the cells of claim 21 under conditions wherein said coding regions are expressed to produce said antibody or said fragment.

24. A method to produce a reshaped antibody that specifically binds human IL-8 or a fragment of said antibody which method comprises culturing the cells of claim 22 under conditions wherein said coding regions are expressed to produce said antibody or said fragment.

25. The method of claim 23 wherein said fragment is $F_{ab}$, $F_{ab'}$, $F_{(ab')2}$ or single chain $F_v$.

26. The method of claim 24 wherein said fragment is $F_{ab}$, $F_{ab'}$, $F_{(ab')2}$ or single chain $F_v$.

27. A polynucleotide which comprises coding regions comprising a nucleotide sequence encoding a V region of a heavy (H) chain of a reshaped antibody that specifically binds human IL-8 wherein the heavy (H) chain of a reshaped antibody comprises the amino acid sequence of SEQ ID NO; 63 (RVHg).

28. The polynucleotide of claim 17 wherein said coding regions further comprise a nucleotide sequence encoding a C region of an H chain of a human antibody.

29. The polynucleotide of claim 27 wherein said coding regions are operably linked to control sequences which effect their expression.

30. The polynucleotide of claim 28 wherein said coding regions are operably linked to control sequences which effect their expression.

31. A recombinant host cell which contains the polynucleotide of claim 29.

32. A recombinant host cell which contains the polynucleotide of claim 30.

33. A method to produce a reshaped antibody that specifically binds human IL-8 or a fragment of said antibody which method comprises culturing the cells of claim 31 under conditions wherein said coding regions are expressed to produce said antibody or said fragment.

34. A method to produce a reshaped antibody that specifically binds human IL-8 or a fragment of said antibody which method comprises culturing the cells of claim 32 under conditions wherein said coding regions are expressed to produce said antibody or said fragment.

35. The method of claim 33 wherein said fragment is $F_{ab}$, $F_{ab'}$, $F_{(ab')2}$ or single chain $F_v$.

36. The method of claim 34 wherein said fragment is $F_{ab}$, $F_{ab'}$, $F_{(ab')2}$ or single chain $F_v$.

* * * * *